(12) United States Patent
Zribi et al.

(10) Patent No.: US 7,104,113 B2
(45) Date of Patent: Sep. 12, 2006

(54) MINIATURIZED MULTI-GAS AND VAPOR SENSOR DEVICES AND ASSOCIATED METHODS OF FABRICATION

(75) Inventors: Anis Zribi, Rexford, NY (US); Wei-Cheng Tian, Niskayuna, NY (US); Gerald Schultz, Brookline, MA (US); Aaron Jay Knobloch, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/719,971

(22) Filed: Nov. 21, 2003

(65) Prior Publication Data

US 2005/0109081 A1 May 26, 2005

(51) Int. Cl.
*G01N 25/00* (2006.01)
*G01N 7/00* (2006.01)
(52) U.S. Cl. .................... 73/31.05; 73/25.05
(58) Field of Classification Search ............... 73/31.05, 73/25.05
See application file for complete search history.

(56) References Cited

U.S. PATENT DOCUMENTS

| | | | | |
|---|---|---|---|---|
| 4,928,513 | A * | 5/1990 | Sugihara et al. | 73/25.03 |
| 5,012,671 | A * | 5/1991 | Yagawara et al. | 73/31.06 |
| 5,451,371 | A | 9/1995 | Zanini-Fisher | |
| 5,659,127 | A | 8/1997 | Shie et al. | |
| 5,804,462 | A * | 9/1998 | Liu et al. | 438/53 |
| 5,866,800 | A * | 2/1999 | Park et al. | 73/31.06 |
| 6,193,413 | B1 | 2/2001 | Lieberman | |
| 6,436,346 | B1* | 8/2002 | Doktycz et al. | 422/51 |
| 6,705,152 | B1* | 3/2004 | Routkevitch et al. | 73/31.05 |
| 2002/0017126 | A1 | 2/2002 | Dimeo et al. | |
| 2002/0026937 | A1* | 3/2002 | Mault | 128/200.24 |
| 2003/0101006 | A1 | 5/2003 | Mansky et al. | |

FOREIGN PATENT DOCUMENTS

| | | |
|---|---|---|
| EP | 0703449 | 9/1995 |
| WO | 0134290 | 11/2000 |

OTHER PUBLICATIONS

"A Substrate for Thin-film Gas Sensors in Microelectronic Technology", U. Dibbern, Sensors and Actuators B (Chemical) Switzerland, vol. 82, No. 1, Mar. 1990.
"Micromachined CMOS Calorimetric Chemical Sensor with On-Chip Low Nose Amplifier", A. Koll et al., MicroElectro Mechanical Systems, 1999, Piscataway, NJ, Jan. 1999, pp. 547-551.
Efremov, M. Yu., "Discrete Periodic Melting Point Observations for Nanostructure Ensembles," Physical Review Letters, vol. 85, No. 17, pp. 3560-3563, Oct. 23, 2000.
Kwan, A.T., "Nanoscale Calorimetry of Isolated Polyethylene Single Crystals," Journal of Polymer Science: Part B: Polymer Physics, vol. 39, pp. 1237-1245, Mar. 22, 2001.

* cited by examiner

*Primary Examiner*—Michael Cygan
(74) *Attorney, Agent, or Firm*—William E. Powell, III; Donald S. Ingraham

(57) ABSTRACT

The invention provides a miniaturized sensor device including a thin film membrane having a first surface and a second surface, one or more resistive thin film heater/thermometer devices disposed directly or indirectly adjacent to the first surface of the thin film membrane, and a frame disposed directly or indirectly adjacent to the second surface of the thin film membrane, wherein one or more internal surfaces of the frame define at least one cell having at least one opening. The sensor device also includes a thin film layer disposed directly or indirectly adjacent to the frame. The sensor device further includes a sensing layer disposed directly or indirectly adjacent to the thin film membrane.

25 Claims, 27 Drawing Sheets

MINIATURIZED MULTI-GAS AND VAPOR SENSOR DEVICES AND ASSOCIATED METHODS OF FABRICATION

FIELD OF THE INVENTION

The invention relates generally to the field of miniaturized sensor devices and platforms and, more specifically, to the field of nano and pico-scale sensor devices and platforms. An aspect of the invention provides robust, high-sensitivity, high-selectivity, high-stability multi-gas and vapor sensor devices, among other sensor devices, and associated methods of fabrication. Variants of the multi-gas and vapor sensor devices of the invention may be used for the in situ measurement of soluble analytes in liquid media. Another aspect of the invention provides a thermally-isolated micro-platform for such microelectromechanical systems (MEMS). A further aspect of the invention provides a design for wide-dynamic range, micro-machined humidity sensor devices, among other sensor devices, that relieves the generated stresses in the associated sensing films caused by sensing film swelling due to the adsorption of water. A still further aspect of the invention provides a protocol for the deposition of self-assembled monolayers (SAMs) as multi-gas and vapor sensing films.

BACKGROUND OF THE INVENTION

The scientific and technological interest in miniaturized gas, humidity, chemical, temperature, and pressure sensor devices has grown in recent years. The need for such devices spans a wide range of industries and applications, such as the medical instrumentation, food and agriculture, paper, automotive, electric appliance, petrochemical, and semiconductor industries, as well as the military, in, for example, gas, humidity, chemical, temperature, and pressure sensing applications. The wide range of environments to which these devices may be exposed severely limits the candidate materials that may be used to build the devices. A number of gas, humidity, chemical, temperature, and pressure sensor devices have been developed and built for specific applications. However, none of these devices demonstrate a suitable combination of the desired robustness, sensitivity, selectivity, stability, size, simplicity, reproducibility, reliability, response time, resistance to contaminants, and longevity. Thus, what are still needed, in general, are multi-gas and vapor sensor devices, among other sensor devices, that exploit the high sensitivity of differential scanning nano and picocalorimetry microelectromechanical systems (MEMS) to heat flow and the unique properties of certain thin films and nano and picoparticles, including their high adsorption potential, high adsorption rate under optimized conditions, high desorption rate under optimized conditions, high chemical stability, and heat release associated with the physisorption of gas and vapor molecules.

Response time, mechanical strength, power consumption, and crosstalk between unit sensor devices are major areas of concern with respect to thermally-sensitive microelectromechanical systems (MEMS), such as gas, humidity, chemical, temperature, and pressure sensor devices, as well as calorimeter and microheater devices, in general. For example, faster response time provides higher sensitivity and greater mechanical strength provides higher reliability. Likewise, lower power consumption is desired for portable and wireless devices and less crosstalk between unit sensor devices provides greater accuracy. Response time and sensitivity are critical in many sensing applications, such as in sensing for warfare agents, measuring low dew points, detecting trace gases, etc., but are difficult to optimize with conventional multi-gas and vapor sensor devices without making sacrifices with respect to other performance parameters. Power consumption and crosstalk between unit sensor devices are both affected by thermal isolation. Typically, thermal isolation has been addressed by fabricating microelectromechanical systems (MEMS) on thin insulating membranes with low heat capacity. However, such thin membranes are fragile, resulting in low yield and reliability problems. Moreover, the peripheries of these thin membranes are typically bonded to a silicon substrate, introducing lateral heat conduction losses. Thus, what are needed are microelectromechanical systems (MEMS) that are built with, for example, low-thermal conductivity regions around the active thin membrane regions, resulting in more robust, high-performance, high-sensitivity microelectromechanical systems (MEMS).

Two additional areas of concern are raised with respect to miniaturized vapor (e.g., humidity) sensor devices, among other sensor devices. First, the polymeric sensing films associated with such vapor sensor devices often become significantly swollen while at relatively high humidity due to their high affinity for water vapor. The swelling of these sensing films generates lateral stresses that impinge upon the thin membranes, potentially breaking them. Second, sensing films having larger surface areas are desired in order to reduce the thickness of the sensing films at a given mass. Reducing the thickness of the sensing films and incorporating nanostructures (e.g., nano-spheres, nano-rods, nano-fibers, etc.) into the sensing materials decreases the diffusion time constant of the water adsorption/desorption, reducing the response time of the vapor sensor devices. Thus, what are needed are micro-machined vapor sensor devices, among other sensor devices, that utilize, for example, high-aspect ratio silicon microstructures etched adjacent to the thin membranes. These silicon microstructures would serve as stress relievers at varying vapor (e.g., humidity) levels and provide both large surface areas for the sensing films, increasing the sensitivity of the vapor sensor devices, and effective heat conduction paths to the microheaters also disposed adjacent to the thin membranes.

BRIEF SUMMARY OF THE INVENTION

In various embodiments, the invention provides robust, high-sensitivity, high-selectivity, high-stability multi-gas and vapor sensor devices and platforms, among other sensor devices and platforms, and associated methods of fabrication. The multi-gas and vapor sensor devices exploit the high sensitivity of differential scanning nano and picocalorimetry microelectromechanical systems (MEMS) to heat flow and the unique properties of certain thin films and nano and picoparticles, such as zeolite thin films and nano and pico-particles, as well as porous ceramics, crosslinked polyelectrolytes, aluminosilicates, and carbon nanotubes, including their high adsorption potential, high adsorption rate under optimized conditions, high desorption rate under optimized conditions, high chemical stability, and heat release associated with the physisorption of gas and vapor molecules. The origins of this heat release are the energy conversions associated directly with the adsorption of a sensed substance, as well as any secondary thermal transitions characteristic of the dry material.

In various embodiments, the invention also provides a thermally-isolated micro-platform for robust, high-performance, high-sensitivity microelectromechanical systems (MEMS). Using various micro-machining techniques, microstructures with low thermal conductivities are incorporated into the peripheries of active thin membrane areas, the thermally-sensitive microelectromechanical systems (MEMS) disposed on either side of the thin membranes. The resulting thermal isolation provides faster response time, greater mechanical strength, lower power consumption, and less crosstalk between unit sensor devices than is possible with a purely thin membrane-based design.

In various embodiments, the invention further provides micro-machined vapor (e.g., humidity) sensor devices, among other sensor devices, that utilize high-aspect ratio silicon microstructures etched adjacent to the thin membranes. These high-aspect ratio silicon microstructures serve as stress relievers due to the large Young's modulus coefficient of silicon. By varying the dimensions of the silicon microstructures, different spring constants may be achieved, accommodating the generated stresses caused by the swelling problems described above at varying vapor/humidity levels. The silicon microstructures provide both large surface areas for the sensing films, increasing the sensitivity of the vapor sensor devices, and effective heat conduction paths to the microheaters also disposed adjacent to the thin membranes. Another method for alleviating the stresses resulting from the adsorption of water vapor by intensely hydrophilic organic polymer materials is provided, involving the creation of a self-assembled monolayer (SAM) with polyelectrolyte functionality on a highly-reticulated substrate of silicon oxide which has been vapor deposited onto the thermally-conductive membrane of a hot plate.

In one specific embodiment of the invention, a miniaturized sensor device includes a thin film membrane having a first surface and a second surface, one or more resistive thin film heater/thermometer devices disposed directly or indirectly adjacent to the first surface of the thin film membrane, and a frame disposed directly or indirectly adjacent to the second surface of the thin film membrane, wherein one or more internal surfaces of the frame define at least one cell having at least one opening. The sensor device also includes a thin film layer disposed directly or indirectly adjacent to the frame. The sensor device further includes a sensing layer disposed directly or indirectly adjacent to the thin film membrane.

In another specific embodiment of the invention, a method for fabricating a miniaturized sensor device includes providing a silicon layer having a first surface and a second surface, depositing a first thin film layer having a first surface and a second surface on the first surface of the silicon layer, and depositing a second thin film layer on the second surface of the silicon layer. The method also includes masking the first surface of the first thin film layer and selectively depositing a sacrificial layer on the first surface of the first thin film layer, wherein the sacrificial layer defines one or more exposed regions of the first surface of the first thin film layer. The method further includes depositing a conductive layer on a surface of the sacrificial layer and the one or more exposed regions of the first surface of the first thin film layer defined by the sacrificial layer and removing the sacrificial layer and a portion of the conductive layer deposited on the surface of the sacrificial layer to form one or more resistive thin film heater/thermometer devices on the first surface of the first thin film layer. The method still further includes selectively removing a portion of the second thin film layer and selectively removing a portion of the silicon layer to form at least one cell, wherein the at least one cell is disposed directly or indirectly adjacent to the second surface of the first thin film layer, and wherein the cell is substantially aligned with the one or more resistive thin film heater/thermometer devices. The method still further includes disposing a sensing layer on the second surface of the first thin film layer.

In a further specific embodiment of the invention, a microelectromechanical system includes a thin film membrane having one or more active membrane areas and one or more inactive membrane areas. The microelectromechanical system also includes one or more resistive thin film heater/thermometer devices disposed directly or indirectly adjacent to the one or more active membrane areas of the thin film membrane. The microelectromechanical system further includes a frame disposed directly or indirectly adjacent to the one or more inactive membrane areas of the thin film membrane. The microelectromechanical system still further includes one or more low-thermal conductivity microstructures disposed between the one or more active membrane areas of the thin film membrane and the one or more inactive membrane areas of the thin film membrane.

In a still further specific embodiment of the invention, a miniaturized sensor device includes a thin film membrane having one or more active membrane areas and one or more inactive membrane areas, one or more resistive thin film heater/thermometer devices disposed directly or indirectly adjacent to the one or more active membrane areas of the thin film membrane, and a frame disposed directly or indirectly adjacent to the one or more inactive membrane areas of the thin film membrane. The sensor device also includes one or more low-thermal conductivity microstructures disposed between the one or more active membrane areas of the thin film membrane and the one or more inactive membrane areas of the thin film membrane. The sensor device further includes one or more stress relief structures disposed directly or indirectly adjacent to the one or more active membrane areas of the thin film membrane. The sensor device still further includes one or more sensing films disposed directly or indirectly adjacent to the one or more stress relief structures.

DETAILED DESCRIPTION OF THE INVENTION

Figure 1:
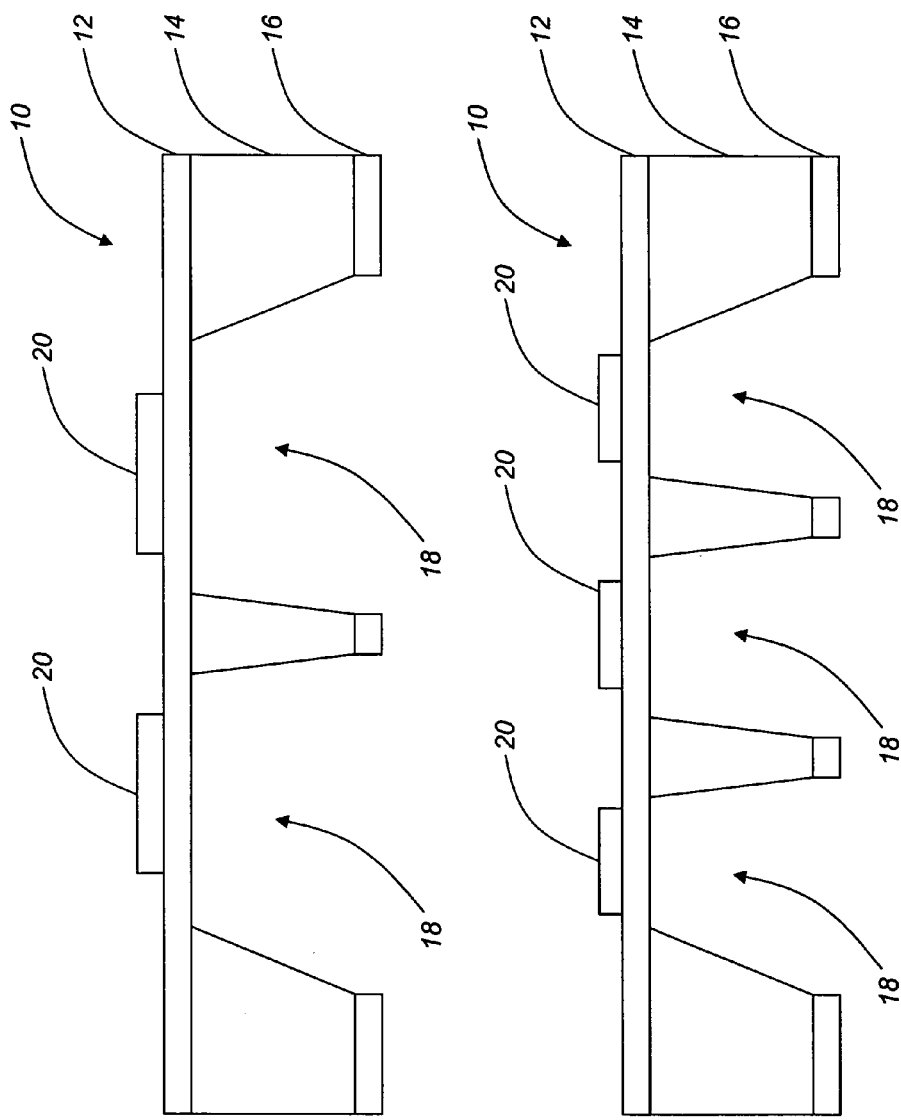
FIG. 1 is a cross-sectional side view of two related embodiments of the sensor device of the invention, the sensor device consisting of a multi-cell ultra high-sensitivity differential scanning calorimeter (UHSDSC), which is a microelectromechanical system (MEMS)

Referring to FIG. 1, the sensor device 10 of the invention, which may be a multi-gas or vapor (e.g., humidity) sensor device, among other sensor devices, consists of a multi-cell ultra high-sensitivity differential scanning calorimeter (UHSDSC), which is a microelectromechanical system (MEMS). The sensor device 10 is fabricated using standard silicon processing techniques, well known to those of ordinary skill in the art. The sensor device 10 includes a thin, thermally-insulating silicon oxinitride ($SiON_x$) membrane 12 disposed directly adjacent to a silicon (Si) frame 14. It should be noted that other suitable materials may replace the silicon oxinitride membrane 12 and/or the silicon frame 14. For example, the silicon oxinitride membrane 12 may be replaced with a silicon, polysilicon, parylene, or polyimide membrane. Preferably, a thin silicon oxinitride layer 16 is also disposed directly adjacent to the silicon frame 14 opposite the silicon oxinitride membrane 12. Again, other suitable materials may replace the silicon oxinitride layer 16. Preferably, the sensor device 10 has an overall length of between about 0.5 mm and about 3 cm, and an overall width of between about 0.5 mm and about 3 cm, although other suitable dimensions may be used. Preferably, the silicon oxinitride membrane 12 has a thickness of between about 50 nm and about 1 micron, although other suitable dimensions may be used. Specifically, the thickness of the silicon oxinitride membrane 12 may be varied depending upon the material(s) used and/or the sensitivity desired. Preferably, the silicon frame 14 has a thickness of between about 50 microns and about 650 microns, although other suitable dimensions may be used. The silicon frame 14 divides the sensor device 10 into two or more cells 18, which are ideally identically symmetric and identical. One of the cells 18 may be used as a reference cell during operation, while the other cells 18 may be used as sensing cells. A plurality of thin film heater/thermometers 20 are disposed directly adjacent to the silicon oxinitride membrane 12 opposite the silicon frame 14. Preferably, the location of each of the plurality of thin film heater/thermometers 20 generally corresponds to each of the two or more cells 18. The plurality of thin film heater/thermometers 20 may be made of platinum (Pt) and/or titanium (Ti), although other suitable materials may be used, such as gold (Au) and/or chromium (Cr), gold and/or nickel (Ni) and/or copper (Cu), aluminum (Al), etc., as well as polysilicon, heavily-doped silicon, silicon carbide, etc. Advantageously, the silicon oxinitride membrane 12 allows rapid heat propagation in the z-direction, to and from the plurality of thin film heater/thermometers 20. It should be noted that the layout and configuration of the sensor device 10 illustrated in FIG. 1 is exemplary only, and is not intended to be limiting. Alternative layouts and configurations may be implemented to fit different geometrical requirements for specific applications.

Figure 2:
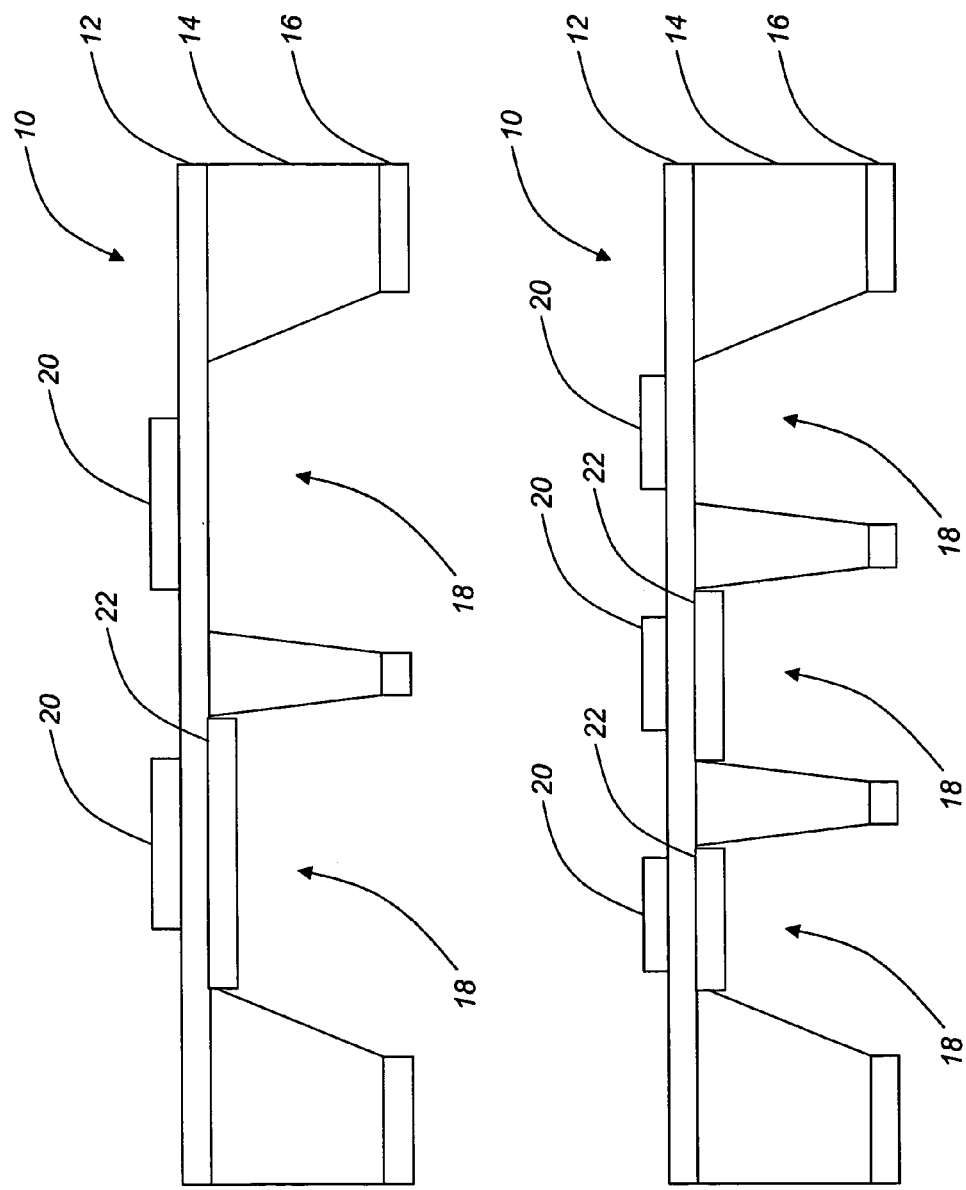
FIG. 2 is a cross-sectional side view of the sensor device of FIG. 1, highlighting the addition of a thin film or nanoparticle layer to one or more cells of the sensor device.

Referring to FIG. 2, a thin film or nanoparticle layer 22 is added to one or more cells 18 of the sensor device 10, directly adjacent to the silicon oxinitride membrane 12 opposite the corresponding thin film heater/thermometer 20. Preferably, the thin film or nanoparticle layer 22 has a thickness of between about 1 nm and about 5 microns, although other suitable dimensions may be used. The thin film or nanoparticle layer 22 consists of a zeolite thin film, a suitable cross-linked organic polyelectrolyte, a self-assembled monolayer of ionic character, or the like, generally comprising materials that generate heat upon the physisorption of gasses and/or vapors. Preferably, the thin film or nanoparticle layer 22 is nano-structured (consisting of spheres, rods, hollow fibers, etc.) such that heat propagates in the z-direction, to and from the plurality of thin film heater/thermometers 20, and not into the surrounding environment. In general, because the thin film or nanoparticle layer 22 consists of a plurality of nanopores, molecules are allowed to travel in and out of the nanopores. Surface saturation would undesirably increase the response time of the sensor device 10. The thin film or nanoparticle layer 22 acts as an interface between a substance to be detected, present in one or both of the cells 18, and the sensor device 10. Upon adsorption of a given amount of this substance onto the surface of the thin film or nanoparticle layer 22, a corresponding amount of heat is released. This heat exchange is measured by the sensor device 10 (operated under power compensation conditions) and subsequently related to the amount of adsorbate in the environment based upon data collected during calibration of the sensor device 10. The adsorbate is driven out of the porous structure of the thin film or nanoparticle layer 22 naturally as its partial pressure in the environment drops. It is possible to accelerate desorption of the adsorbate from the porous structure of the thin film or nanoparticle layer 22 by pulse heating the thin film or nanoparticle layer 22 without damaging its structure. Preferably, the microstructure of the thin film or nanoparticle layer 22 and its pore dimensions are customized to ensure the high selectivity of the sensor device 10 towards a specific adsorbate. In addition, active selectivity may be achieved by operating the sensor device 10 in a desorption mode. In this mode, heat is applied to the sensing material by flowing a direct or modulated current through the thin film heater/thermometers 20, leading to the desorption of all adsorbed species at specific temperatures. The desorption temperature is used to discriminate against undesired adsorbates and contaminants. The sensor device 10 is operated under power compensation conditions as, under these conditions, the sensor device 10 is least prone to picking-up noise signals. In the power compensation mode, a reference power source compensates for any temperature changes that the reference thin film heater/thermometer 20 experiences relative to the sensing thin film heater/thermometer 20 due to heat exchange with the thin film or nanoparticle layer 22.

Figure 3:
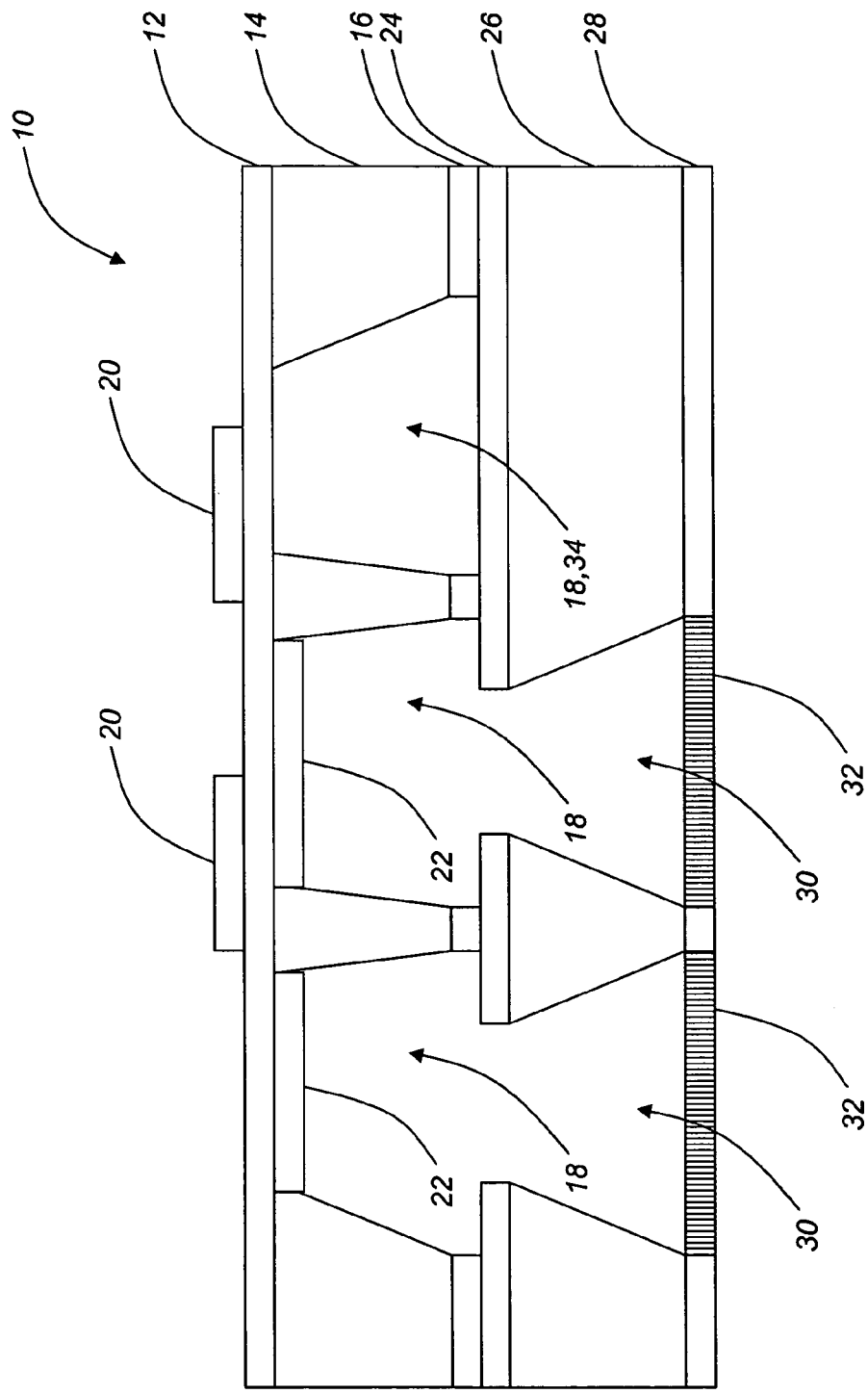
FIG. 3 is a cross-sectional side view of another embodiment of the sensor device of the invention, highlighting the use of one or more grids operable for keeping particulates and/or contaminants away from the one or more thin film or nanoparticle layers of FIG. 2.

Referring to FIG. 3, in an alternative embodiment of the invention, the sensor device 10 is equipped with a built-in protection mechanism designed to prevent the "locking" of the pores of the thin film or nanoparticle layer 22. In general, the sensor device 10 described above is disposed directly adjacent to an additional silicon oxinitride membrane 24, an additional silicon frame 26, and an additional silicon oxinitride layer 28 via bonding in a controlled environment. As before, other suitable materials may replace the additional silicon oxinitride membrane 24, the additional silicon frame 26, and the additional silicon oxinitride layer 28. Preferably, the additional silicon oxinitride membrane 24, the additional silicon frame 26, and the additional silicon oxinitride layer 28 collectively define an additional cell 30. The opening of this additional cell 30 to the environment is guarded by a grid 32 operable for keeping particulates and/or contaminants away from the thin film or nanoparticle layer 22. The grid 32 may be fabricated using standard silicon processing and lithography techniques, well known to those of ordinary skill in the art. Advantageously, the presence of the additional silicon oxinitride membrane 24 isolates one of the original cells 18,34 from the environment, which may then be maintained with an atmosphere of dry inert gas (e.g., air, nitrogen, etc.).

Figure 4:
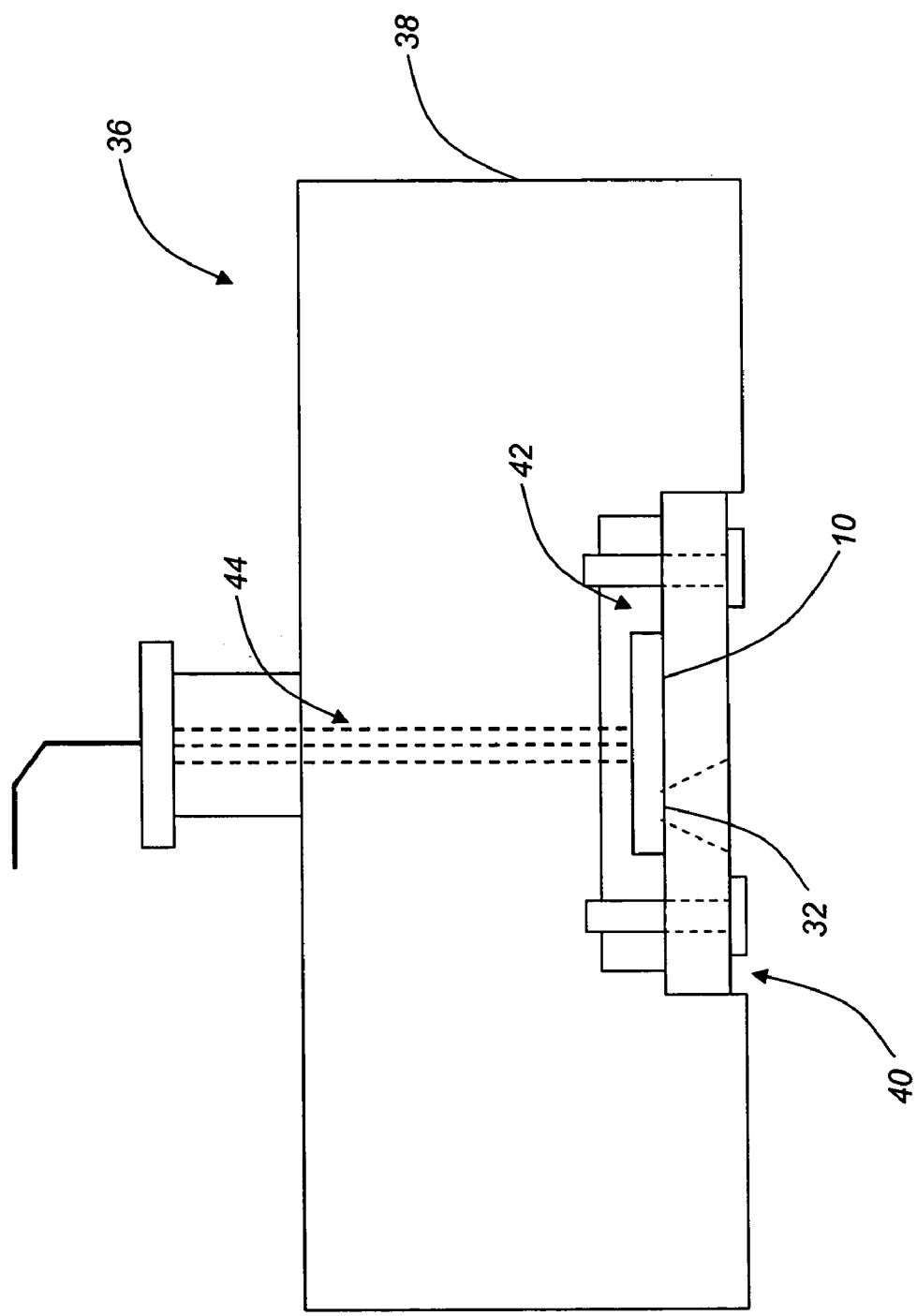
FIG. 4 is a cross-sectional side view of one embodiment of a packaging assembly for the sensor devices of FIGS. 1–3.

In general, the sensor devices 10 (FIGS. 1–3) of the invention require short heat transfer paths between the thin film or nanoparticle layer(s) 22 (FIGS. 2 and 3) and the thin film heater/thermometer(s) 20 (FIGS. 1–3), as well as minimal heat losses to the environment. While the former concern is addressed through the use of the thin silicon oxinitride membrane 12 (FIGS. 1–3), the latter concern must be addressed through the packaging of the sensor devices 10. Referring to FIG. 4, an exemplary packaging assembly 36 includes a ceramic block 38, such as a Maycor block or the like, having a recessed cavity 40 suitable for containing the sensor device 10 being used. The sensor device 10 is secured within the recessed cavity 40 such that at least one cell 18 (FIGS. 1–3) of the sensor device 10 is exposed to the environment. As described above, a grid 32 (see also FIG. 3) may be used to keep particulates and/or contaminants away from the thin film or nanoparticle layer 22. Preferably, the volume 42 of the recessed cavity 40 surrounding the sensor device 10 is filled with dry air or an inert gas in order to keep certain components of the packaging assembly 36 from oxidizing. For example, a nitrogen ($N_2$) atmosphere may be used. A plurality of copper-beryllium (Cu—Be) spring-loaded probes 44 or the like pass through the ceramic block 38 and come into electrical contact with the thin film heater/thermometer(s) 20 of the sensor device 10. Advantageously, this and similar packaging assemblies ensure high thermal resistance between the thin film heater/thermometer(s) 20 and the environment. Thus, a high signal-to-noise ratio may be achieved.

Figure 5:
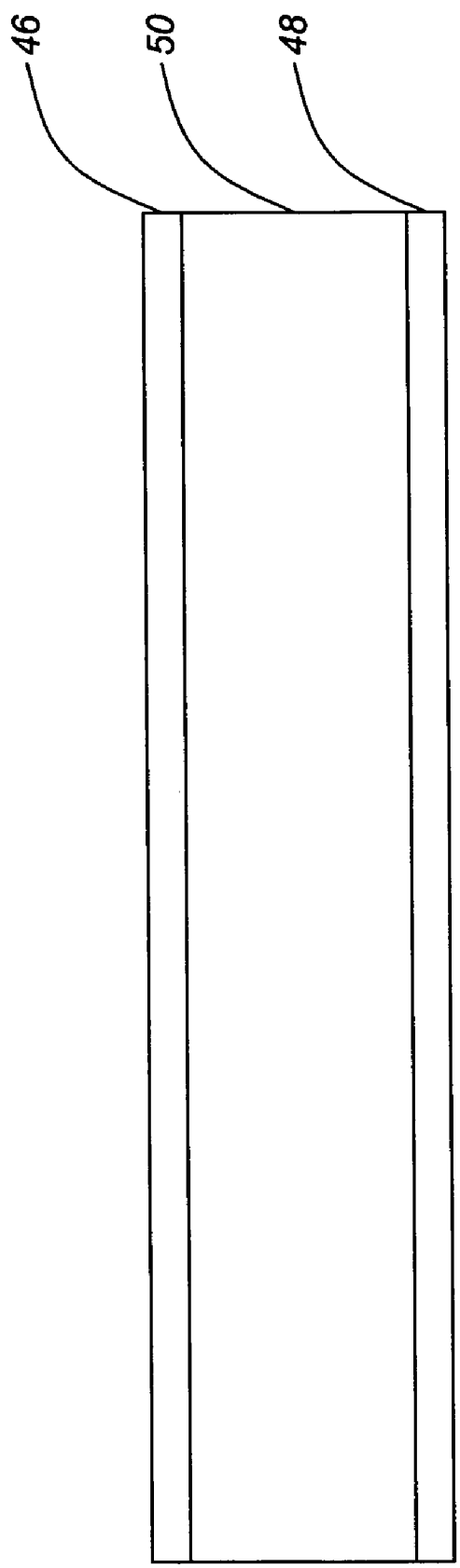
FIG. 5 is a cross-sectional side view illustrating a first step in the fabrication of the sensor device of FIG. 1.

Referring to FIG. 5, the first step in the fabrication of the sensor device 10 (FIGS. 1 and 2) of the invention includes the low stress deposition of a first thin film amorphous silicon oxinitride layer 46 (eventually becoming what is referred to above as the silicon oxinitride membrane 12 (FIGS. 1 and 2)) and a second thin film amorphous silicon oxinitride layer 48 (eventually becoming what is referred to above as the silicon oxinitride layer 16 (FIGS. 1 and 2)) on opposing sides of a silicon layer or wafer 50 (eventually becoming what is referred to above as the silicon frame 14 (FIGS. 1 and 2)). Preferably, the silicon layer 50 consists of single-crystal silicon oriented in the <100> or <110> direction. As described above, however, other suitable materials may replace the first silicon oxinitride layer 46, the second silicon oxinitride layer 48, and the silicon layer 50. As used herein, "low stress deposition" refers to deposition wherein the stress level in the first silicon oxinitride layer 46 corresponds to tensile stresses and is adjusted to compensate for the compressive stresses applied by the sensing material to the membrane.

Figure 6:
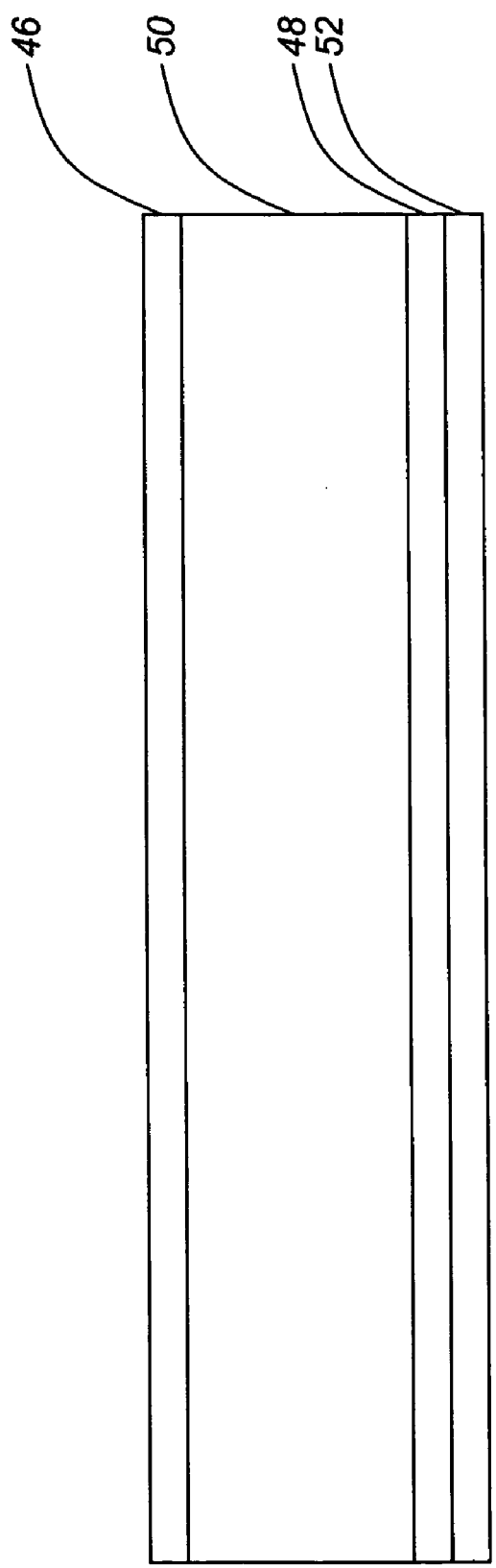
FIG. 6 is a cross-sectional side view illustrating a second step in the fabrication of the sensor device of FIG. 1.

Referring to FIG. 6, the second step in the fabrication of the sensor device 10 includes depositing and baking a photoresist (PR) coating 52 on the surface of the second silicon oxinitride layer 48. The photoresist (PR) coating 52 protects the second silicon oxinitride layer 48 from scratching during subsequent processing.

Figure 7:
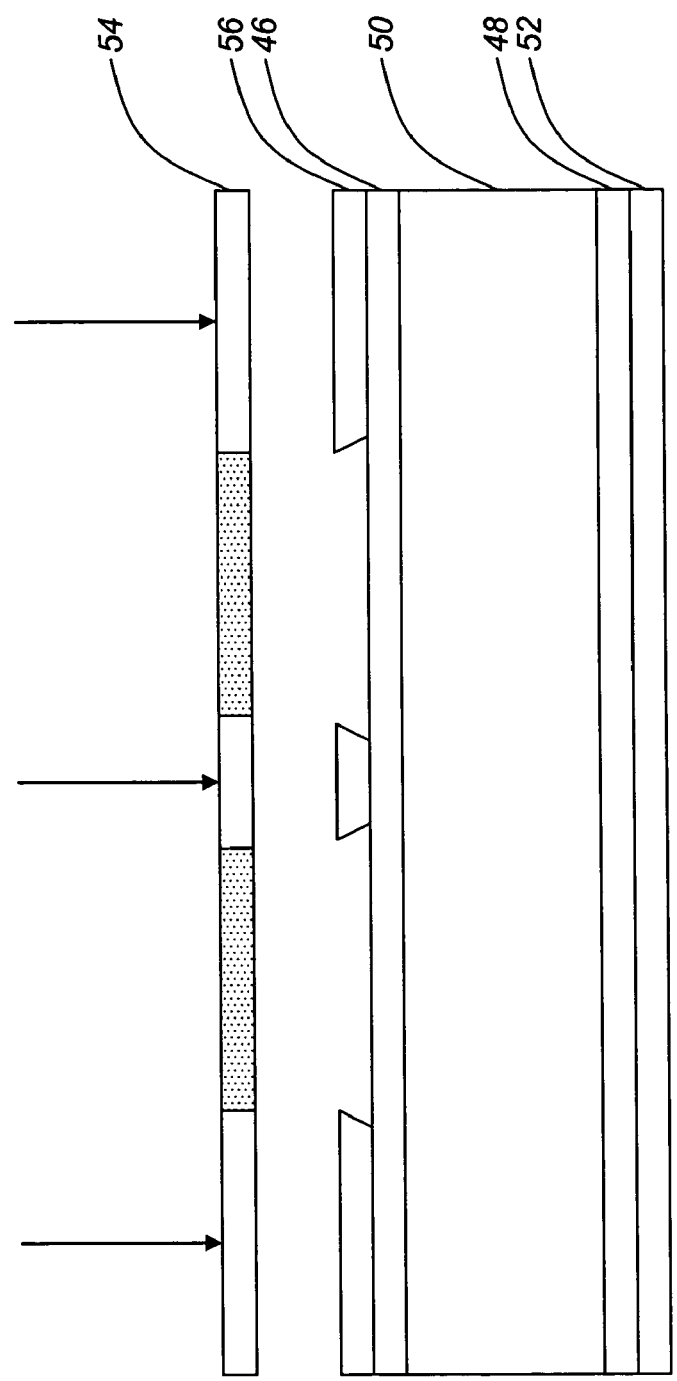
FIG. 7 is a cross-sectional side view illustrating a third step in the fabrication of the sensor device of FIG. 1.

Referring to FIG. 7, the third step in the fabrication of the sensor device 10 is a lithography and image reversal step. A mask 54 is disposed adjacent to the surface of the first silicon oxinitride layer 46 and a photoresist (PR) layer 56 is selectively spun onto the surface of the first silicon oxinitride layer 46. Preferably, the photoresist (PR) layer 56 has a thickness that is about three (3) times as thick as a metal layer that will subsequently be deposited (about 0.5 microns). The image is reversed using an ammonia diffusion bake, flood exposure, and development of the photoresist (PR).

Figure 8:
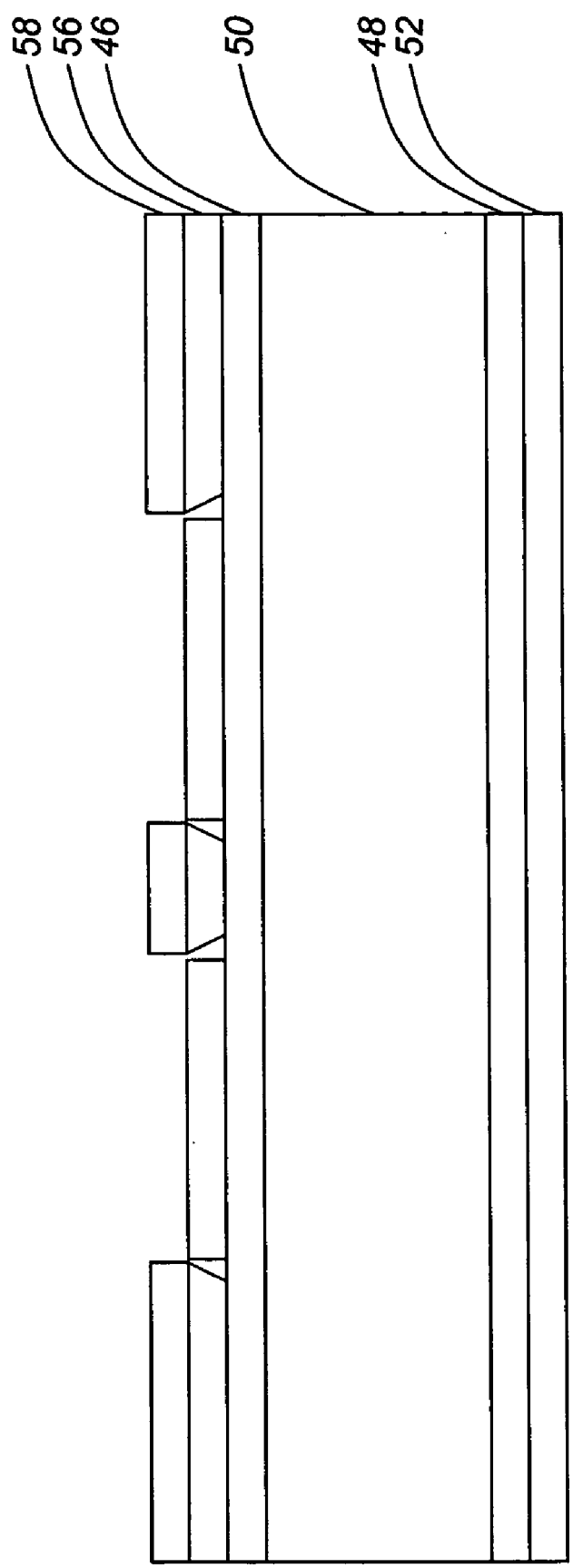
FIG. 8 is a cross-sectional side view illustrating a fourth step in the fabrication of the sensor device of FIG. 1.

Referring to FIG. 8, the fourth step in the fabrication of the sensor device 10 includes evaporating a metal layer 58 onto the surface of the photoresist (PR) layer 56 and the exposed portions of the first silicon oxinitride layer 46. The metal layer 58 may include, for example, platinum, gold (Au), nickel (Ni), or aluminum (Al). Alternatively, the metal layer 58 may be replaced with a polysilicon layer, a heavily-doped silicon layer, or a layer of any other conductive material having a tunable resistance in order to modify its sensitivity. Optionally, the metal layer 58 consists of a titanium layer (about 4 nm thick, for example), which acts as a bonding layer, and a platinum layer (about 50 nm thick, for example).

Figure 9:
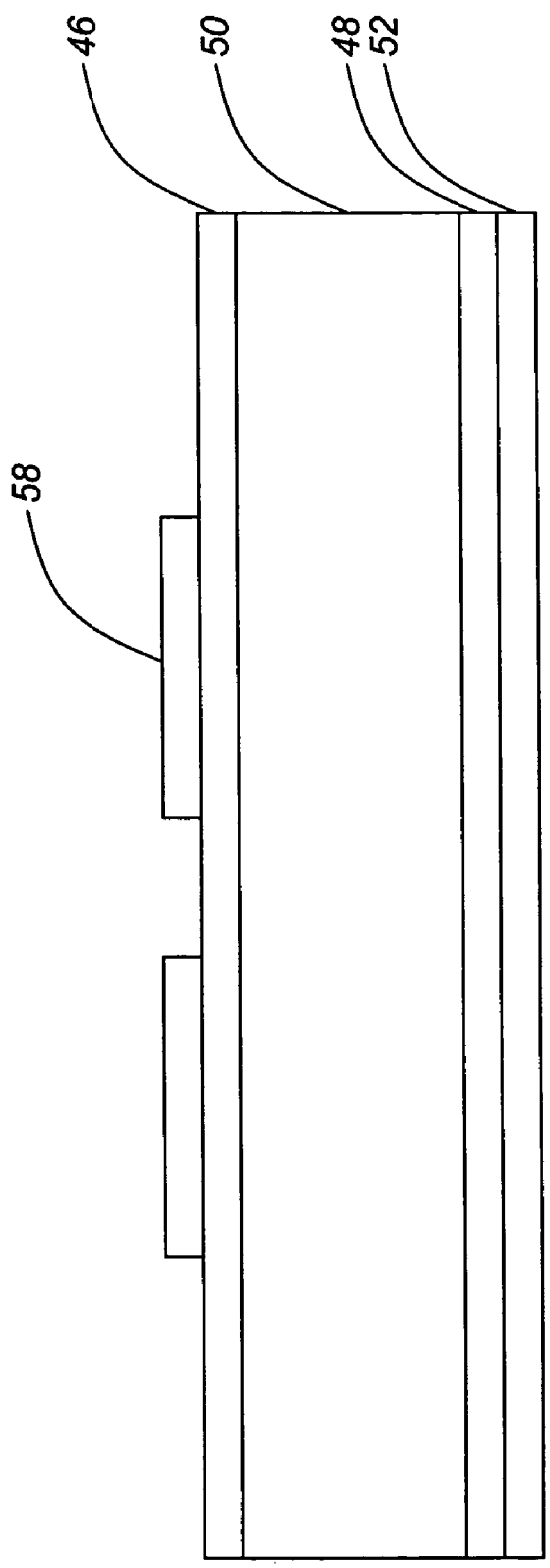
FIG. 9 is a cross-sectional side view illustrating a fifth step in the fabrication of the sensor device of FIG. 1.

Referring to FIG. 9, the fifth step in the fabrication of the sensor device 10 includes using acetone or the like and an ultrasound bath or the like to lift-off the photoresist (PR) layer 56 and selected portions of the metal layer 58, forming the plurality of thin film heater/thermometers 20 (FIGS. 1 and 2) described above.

Figure 10:
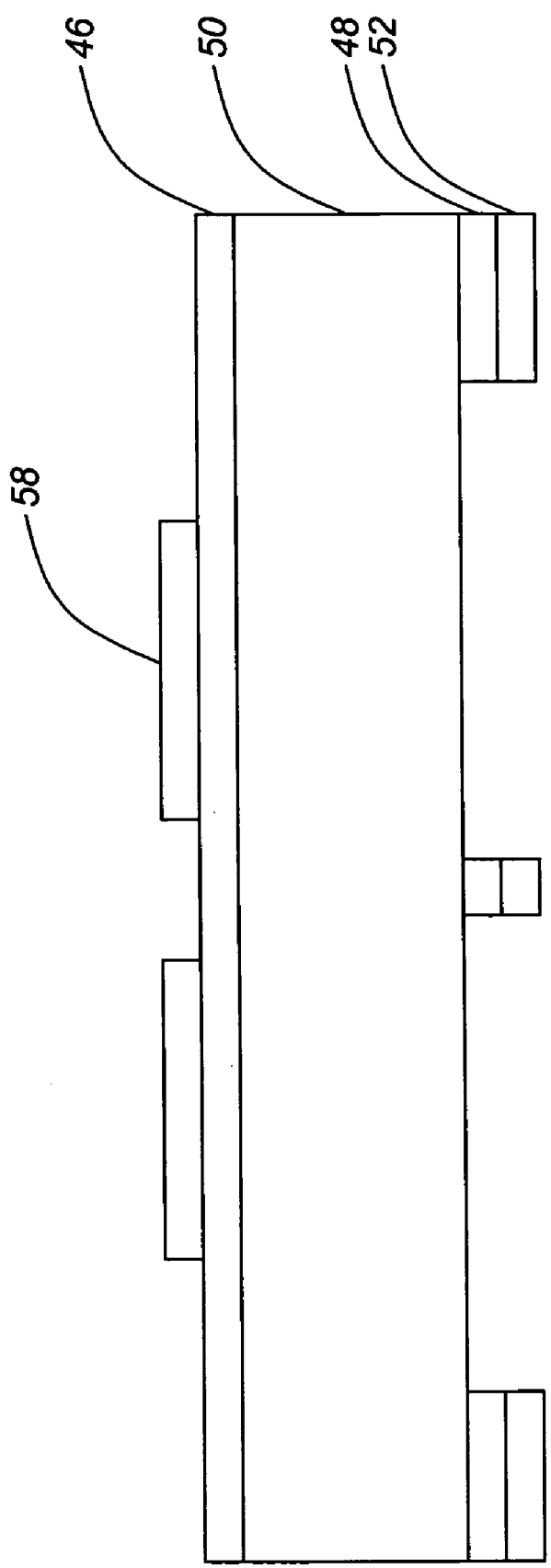
FIG. 10 is a cross-sectional side view illustrating a sixth step in the fabrication of the sensor device of FIG. 1.

Referring to FIG. 10, the sixth step in the fabrication of the sensor device 10 includes performing backside optical lithography and a dielectric etch to selectively remove a portion of the photoresist (PR) coating 52 and the second silicon oxinitride layer 48, exposing a portion of the silicon layer 50.

Figure 11:
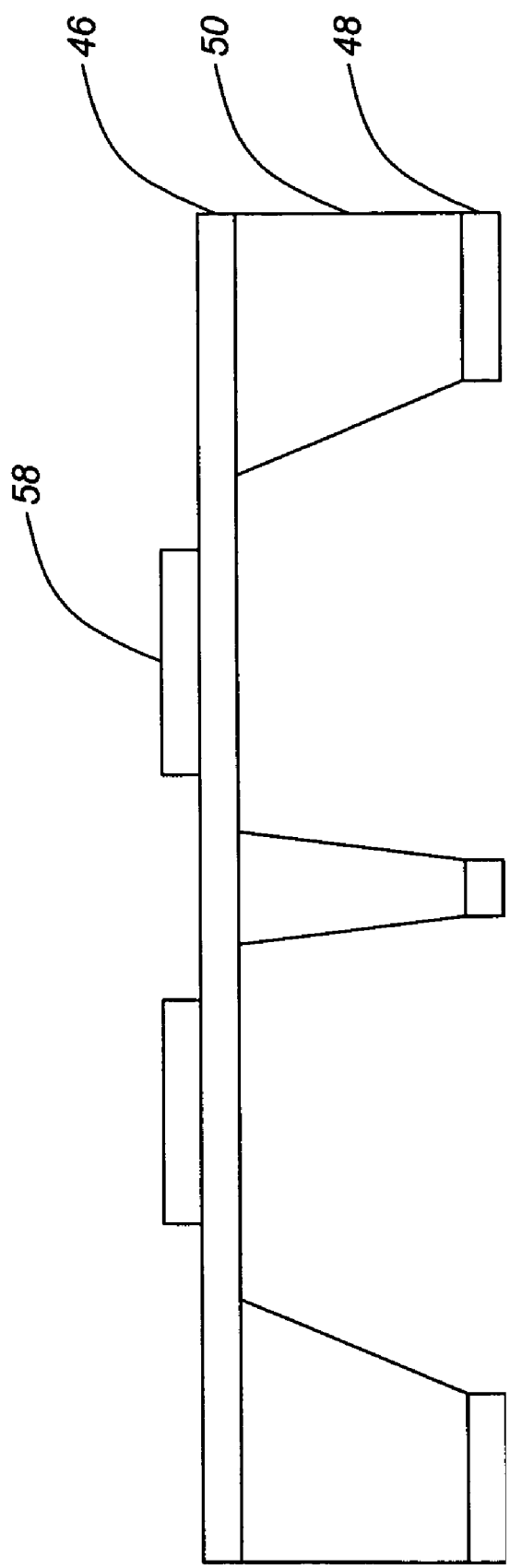
FIG. 11 is a cross-sectional side view illustrating a seventh step in the fabrication of the sensor device of FIG. 1.

Referring to FIG. 11, the seventh step in the fabrication of the sensor device 10 includes performing a potassium hydroxide (KOH), ethylene diamine pyrocatechol (EDP), or deep reactive ion (DRI) etch to selectively remove the remaining portions of the photoresist (PR) coating 52 and a portion of the silicon layer 50, forming the silicon oxinitride membrane 12, the silicon frame 14, and one or more of the cells 18 (FIGS. 1 and 2) described above. At this point, the thin film or nanoparticle layer 22 (FIG. 2) may be deposited or grown directly on the surface of the silicon oxinitride membrane 12 within the one or more cells 18.

Figure 12:
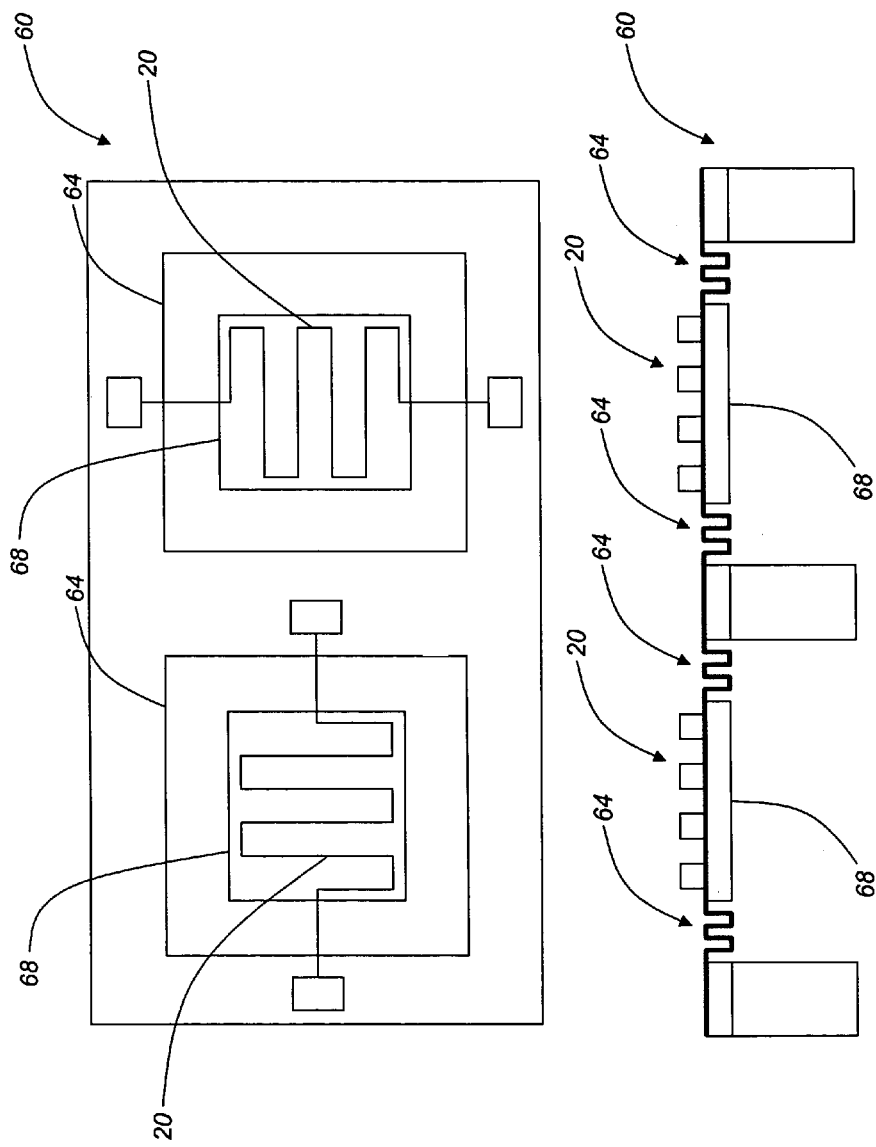
FIG. 12 is a top planar view and a cross-sectional side view of one embodiment of the thermally-isolated micro-platform for microelectromechanical systems (MEMS) of the invention, highlighting the use of a trench refill approach using a dielectric material and high-aspect ratio trenches (HARTs) or grids.
Figure 18:
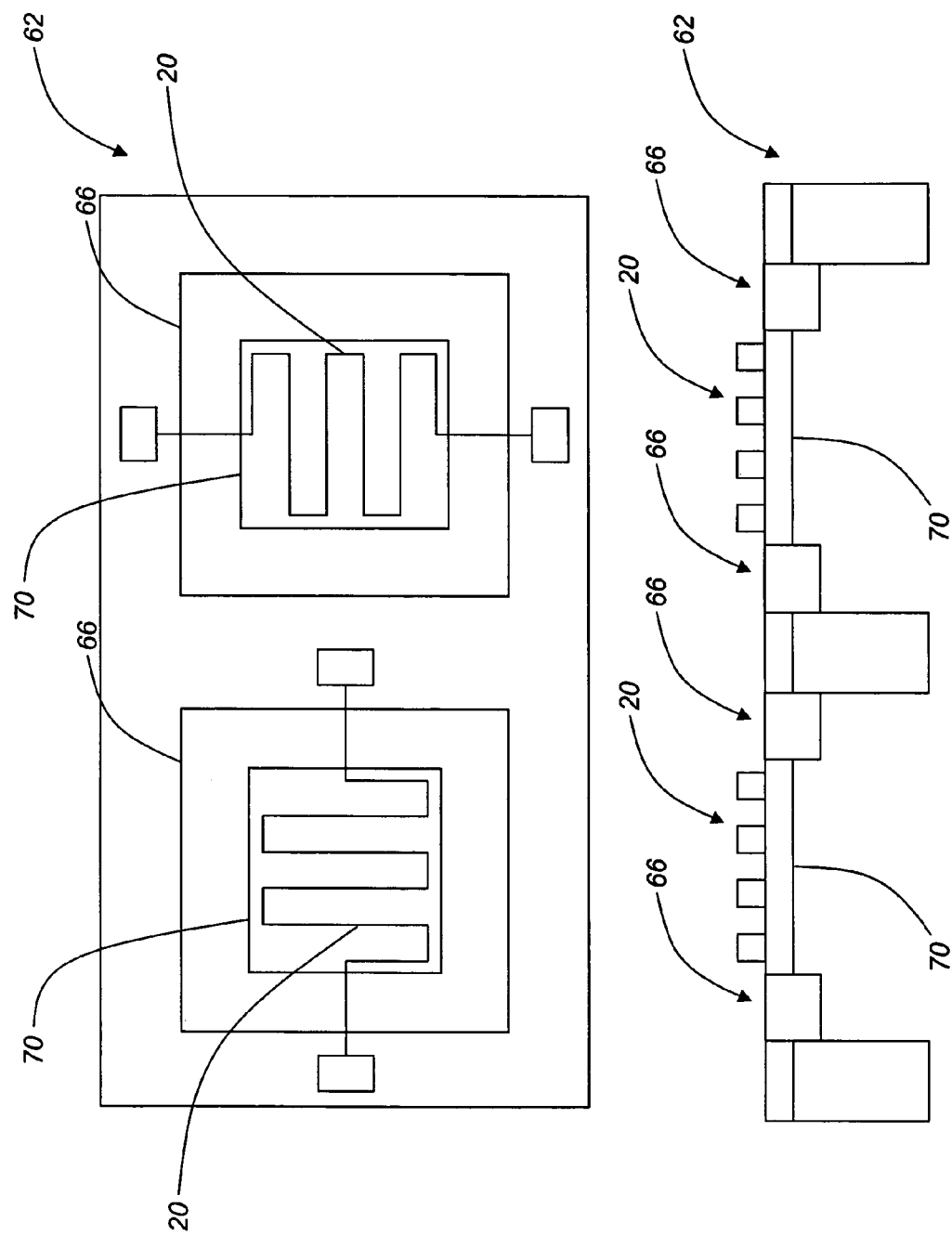
FIG. 18 is a top planar view and a cross-sectional side view of another embodiment of the thermally-isolated micro-platform for microelectromechanical systems (MEMS) of the invention, highlighting the use of a thick oxide approach using the thermal oxidation of high-aspect ratio trenches (HARTs) or grids.

Referring to FIGS. 12 and 18, the thermally-isolated micro-platforms 60,62 for microelectromechanical systems (MEMS) of the invention include a plurality of microstructures 64,66 with large thermal resistances built on the peripheries of active membrane areas 68,70. These microstructures 64,66 are operable for reducing lateral heat conduction, reducing heat loss to the environment, and increase the mechanical strength of the microelectromechanical systems (MEMS) into which they are incorporated. Enhanced thermal isolation leads to enhanced sensitivity, faster response time, and decreased power consumption for the microelectromechanical systems (MEMS), which may include, for example, the multi-gas or vapor sensor devices 10 (FIGS. 1–3) described above, among other sensor devices. Two approaches are described for fabricating the thermally-isolated micro-platforms 60,62 for microelectromechanical systems (MEMS) of the invention: (1) a micro/nanostructure refill approach using a dielectric material with low thermal conductivity and high-aspect ratio micro/nanostructures, such as trenches, grids, posts, vias, or pores, and (2) a thick oxide approach using the thermal oxidation of high-aspect ratio micro/nanostructures, such as those described above.

Figure 13:
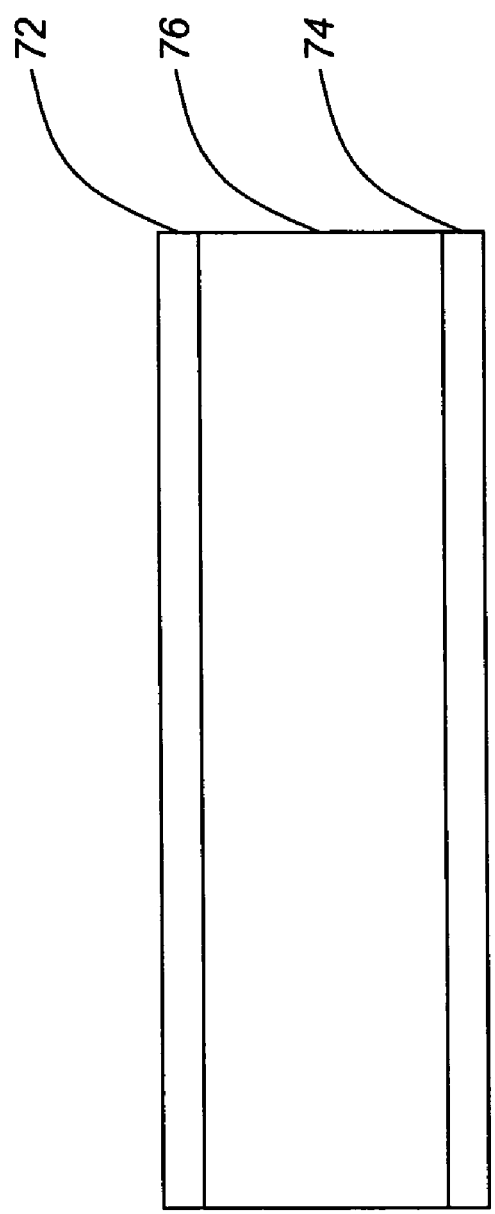
FIG. 13 is a cross-sectional side view illustrating the first step of the trench refill approach using a dielectric material and high-aspect ratio trenches (HARTs) or grids of FIG. 12.

Referring to FIG. 13, the first step of the trench refill approach using a dielectric material and high-aspect ratio trenches (HARTs) or grids includes the deposition of a first thin film dielectric layer 72, such as a first thin film silicon oxinitride layer or the like, and a second thin film dielectric layer 74, such as a second thin film silicon oxinitride layer or the like, on opposing sides of a silicon layer or wafer 76 or the like. As described above, any suitable materials may be used for the first thin film dielectric layer 72, the second thin film dielectric layer 74, and the silicon layer or wafer 76. Preferably, the first thin film dielectric layer 72 has a thickness of between about 0.1 microns and about 5 microns, the second thin film dielectric layer 74 has a thickness of between about 0.1 microns and about 5 microns, and the silicon layer or wafer 76 has a thickness of between about 100 microns and about 1,000 microns. The first thin film dielectric layer 72 and the second thin film dielectric layer 74 may be deposited simultaneously and have the same thickness. The thickness of the first thin film dielectric layer 72 and the second thin film dielectric layer 74 is determined by the specifications of the given multi-gas or vapor sensor device 10 (FIGS. 1–3). For example, if the first thin film dielectric layer 72 is for building membrane, at a given area, a thicker membrane provides a higher natural frequency at resonance.

Figure 14:
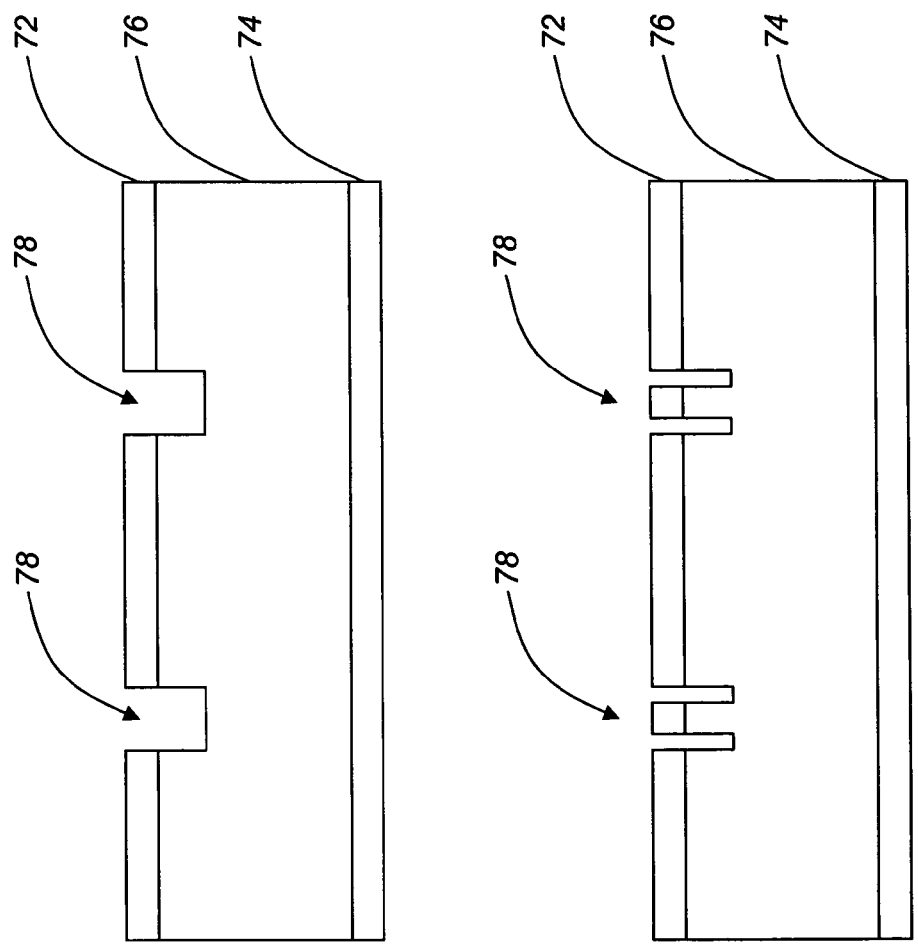
FIG. 14 is a cross-sectional side view illustrating the second step of the trench refill approach using a dielectric material and high-aspect ratio trenches (HARTs) or grids of FIG. 12.

Referring to FIG. 14, the second step of the trench refill approach using a dielectric material and high-aspect ratio trenches (HARTs) or grids includes etching the high-aspect ratio trenches (HARTs) or grids 78 (also referred to generally as the high-aspect ratio micro/nanostructures 78) in a portion of the first thin film dielectric layer 72 and the silicon layer or wafer 76 using a first mask (not shown). Preferably, each of the high-aspect ratio micro/nanostructures 78 has a width of between about 0.01 microns and about 10 microns, a depth of between about 1 micron and about 500 microns, and an aspect ratio of between about 1 and about 100. These high-aspect ratio micro/nanostructures 78 define and surround the active membrane area(s) 68 (FIG. 12). The high-aspect ratio micro/nanostructures 78 may be fabricated using either wet etching (e.g., KOH etching on <110> silicon (Si) or electrochemical etching) or dry etching (e.g., DRIE). The aspect ratio is limited by the etching technology and is preferably as high as possible. Refilled dielectric on the sidewalls may touch at the resulting opening and close the trench to form a void. This void may be vacuum-sealed if the dielectric deposition is performed in a vacuum.

Figure 15:
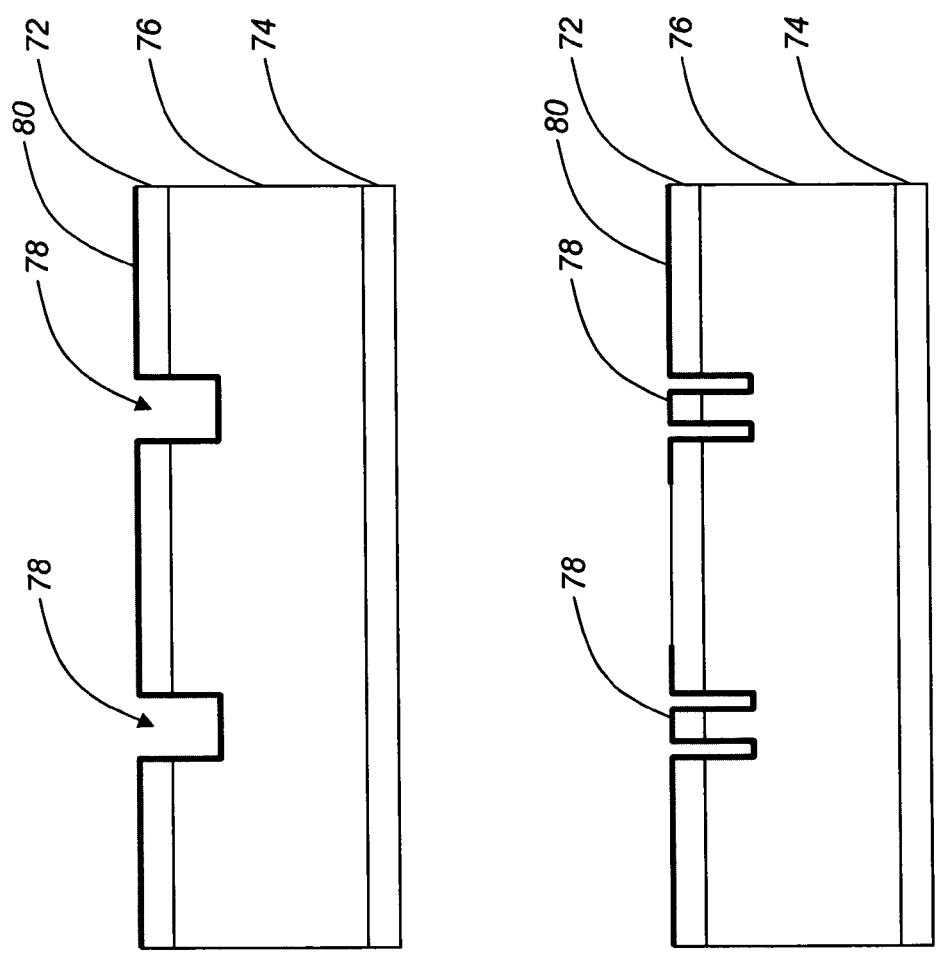
FIG. 15 is a cross-sectional side view illustrating the third step of the trench refill approach using a dielectric material and high-aspect ratio trenches (HARTs) or grids of FIG. 12.

Referring to FIG. 15, the third step of the trench refill approach using a dielectric material and high-aspect ratio trenches (HARTs) or grids includes the removal of the first thin film dielectric layer 72 outside of the active membrane area(s) 68 (FIG. 12) using a second mask (not shown) and the selective deposition of a dielectric layer 80 on the remaining portions of the first thin film dielectric layer 72 and the exposed portions of the silicon layer or wafer 76 using, for example, a low-pressure chemical vapor deposition (LPCVD), plasma-enhanced chemical vapor deposition (PECVD), or spin-on coating technique, well known to those of ordinary skill in the art. Preferably, the dielectric layer 80 has a thickness of between about 0.5 microns and about 10 microns. The second mask may not be needed if the first thin film dielectric layer 72 is thin enough and does not alter the sensor device 10 (FIGS. 1–3) specifications, such as the natural frequency of the membrane at resonance. The dielectric layer 80 may include an oxide, a glass, a polyimide, a polymer, a nitride, any other suitable low-thermal conductivity material, or any suitable combination thereof. Advantageously, the spin-on coating technique provides a low-temperature process, thus reducing undesirable residual thermal stresses in the first thin film dielectric layer 72. Additionally, an oxide/nitride/oxide or nitride/oxide/nitride may be deposited for stress compensation to reduce undesirable residual thermal stresses.

Figure 16:
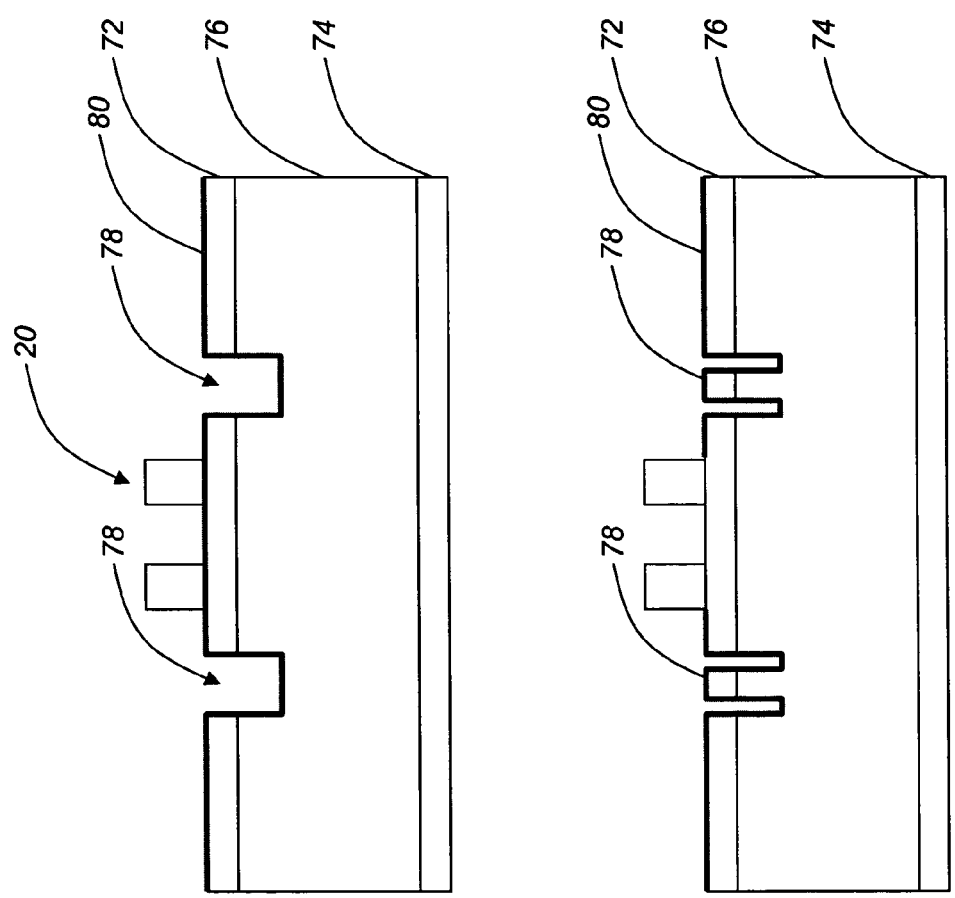
FIG. 16 is a cross-sectional side view illustrating the fourth step of the trench refill approach using a dielectric material and high-aspect ratio trenches (HARTs) or grids of FIG. 12.

Referring to FIG. 16, the fourth step of the trench refill approach using a dielectric material and high-aspect ratio trenches (HARTs) or grids includes depositing and patterning the plurality of thin film heater/thermometers, as described above, on or adjacent to the surface of the dielectric layer 80, adjacent to the surface of the first thin film dielectric layer 72. This is done using a third mask (not shown). As described above, the plurality of thin film heater/thermometers 20 may include a metal, polysilicon, heavily-doped silicon, silicon carbide, or the like.

Figure 17:
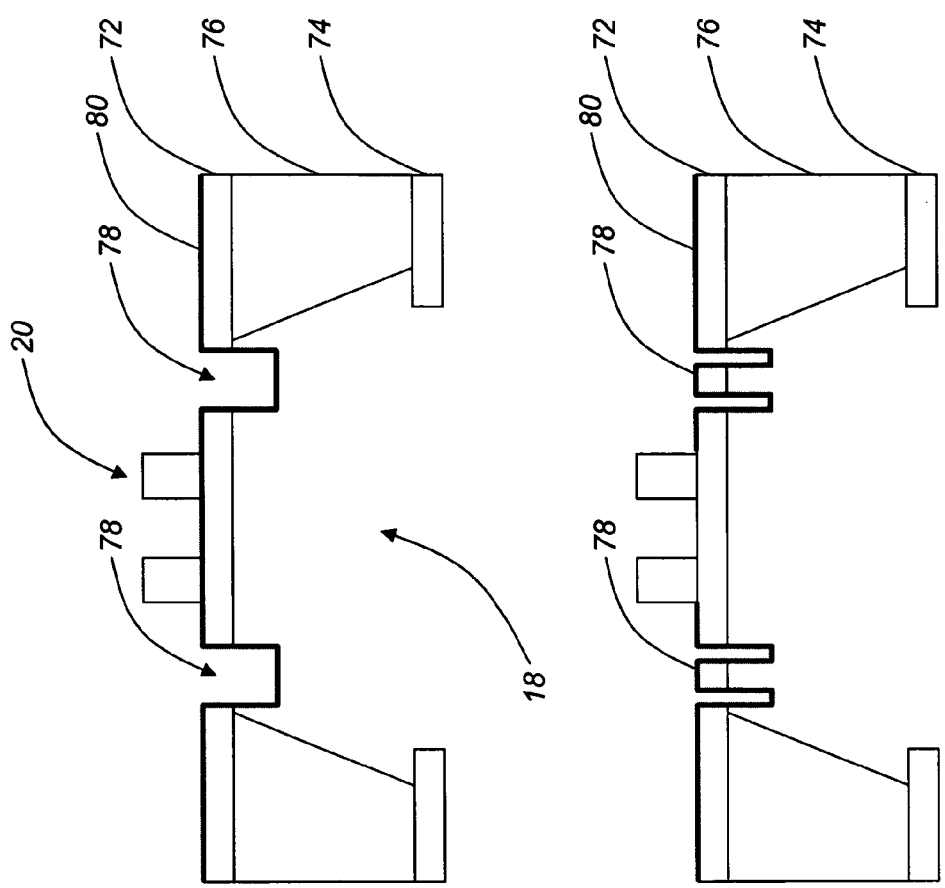
FIG. 17 is a cross-sectional side view illustrating the fifth step of the trench refill approach using a dielectric material and high-aspect ratio trenches (HARTs) or grids of FIG. 12.

Referring to FIG. 17, the fifth step of the trench refill approach using a dielectric material and high-aspect ratio trenches (HARTs) or grids includes patterning and selectively etching the second thin film dielectric layer 74 and the silicon layer 76 to form one or more of cells 18 described above. This is done using a fourth mask (not shown). The etching process may comprise a wet and/or dry etching technique, such as potassium hydroxide (KOH) etching, tetramethylammonium hydroxide (TMAH) etching, ethylene diamine pyrocatechol (EDP) etching, and/or deep reactive ion (DRI) etching.

Figure 19:
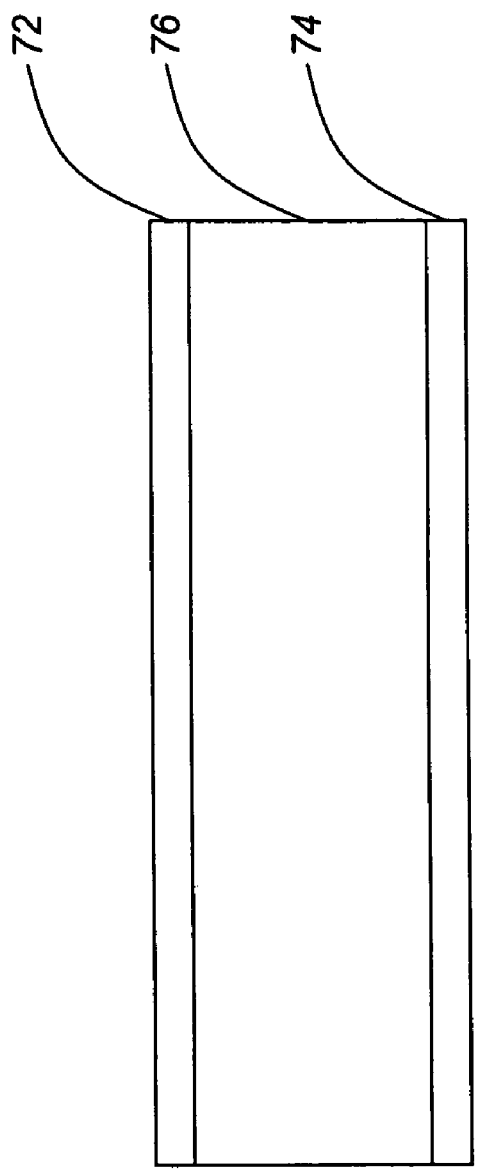
FIG. 19 is a cross-sectional side view illustrating the first step of the thick oxide approach using the thermal oxidation of high-aspect ratio trenches (HARTs) or grids of FIG. 18.

Referring to FIG. 19, the first step of the thick oxide approach using the thermal oxidation of high-aspect ratio trenches (HARTs) or grids includes the deposition of a first thin film dielectric layer 72, such as a first thin film silicon oxinitride layer or the like, and a second thin film dielectric layer 74, such as a second thin film silicon oxinitride layer or the like, on opposing sides of a silicon layer or wafer 76 or the like. As described above, any suitable materials may be used for the first thin film dielectric layer 72, the second thin film dielectric layer 74, and the silicon layer or wafer 76. Preferably, the first thin film dielectric layer 72 has a thickness of between about 0.1 microns and about 5 microns, the second thin film dielectric layer 74 has a thickness of between about 0.1 microns and about 5 microns, and the silicon layer or wafer 76 has a thickness of between about 100 microns and about 1,000 microns. The first thin film dielectric layer 72 and the second thin film dielectric layer 74 may be deposited simultaneously and have the same thickness. The thickness of the first thin film dielectric layer 72 and the second thin film dielectric layer 74 is determined by the specifications of the given multi-gas or vapor sensor device 10 (FIGS. 1–3). For example, if the first thin film dielectric layer 72 is for building membrane, at a given area, a thicker membrane provides a higher natural frequency at resonance.

Figure 20:
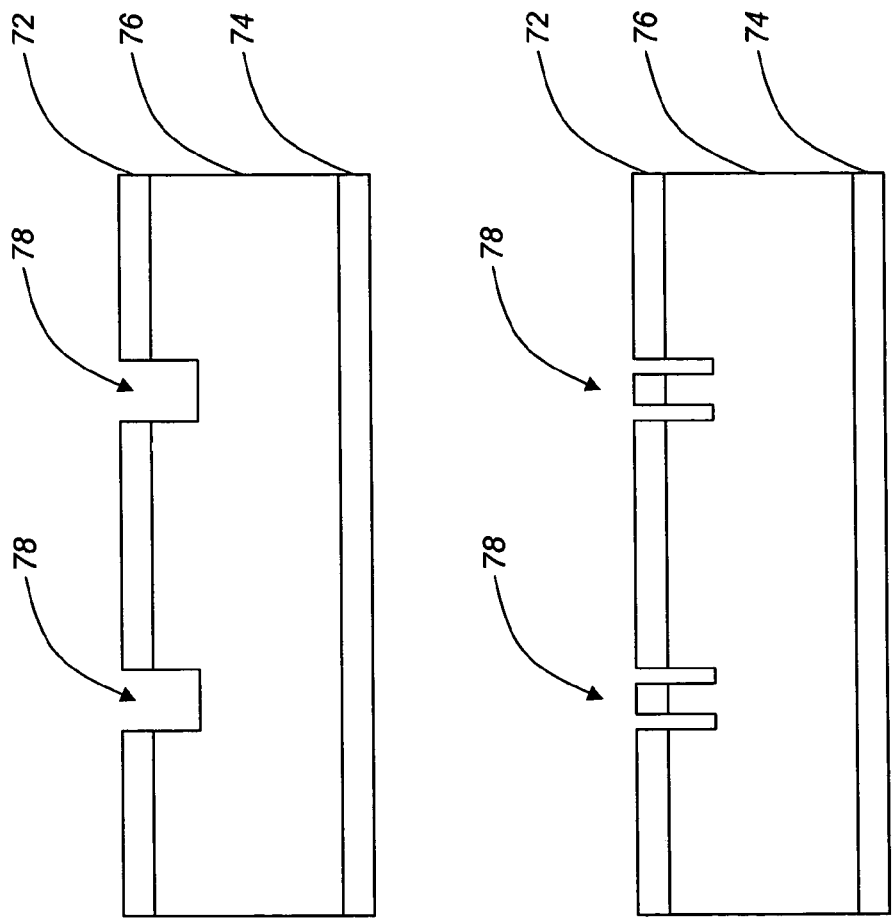
FIG. 20 is a cross-sectional side view illustrating the second step of the thick oxide approach using the thermal oxidation of high-aspect ratio trenches (HARTs) or grids of FIG. 18.

Referring to FIG. 20, the second step of the thick oxide approach using the thermal oxidation of high-aspect ratio trenches (HARTs) or grids includes etching the high-aspect ratio trenches (HARTs) or grids 78 in a portion of the first thin film dielectric layer 72 and the silicon layer or wafer 76 using a first mask (not shown). Preferably, each of the high-aspect ratio trenches (HARTs) or grids 78 has a width of between about 1 micron and about 10 microns, a depth of between about 1 micron and about 500 microns, and an aspect ratio of between about 1 and about 50. The spacing between the high-aspect ratio micro/nanostructures 78 is of importance and should be less than about 1.08 microns in order to seal the high-aspect ratio micro/nanostructures 78 as the final oxide thickness is approximately 54% above the original surface of the silicon and approximately 46% below the original surface. However, this thick oxide approach may be combined with the trench refill approach to seal the gap if small spacing cannot be achieved. The high-aspect ratio micro/nanostructures 78 define and surround the active membrane area(s) 68 (FIG. 18). The high-aspect ratio micro/nanostructures 78 may be fabricated using either wet etching (e.g., KOH etching on <110> silicon (Si) or electrochemical etching) or dry etching (e.g., DRIE). The aspect ratio is limited by the etching technology and is preferably as high as possible.

Figure 21:
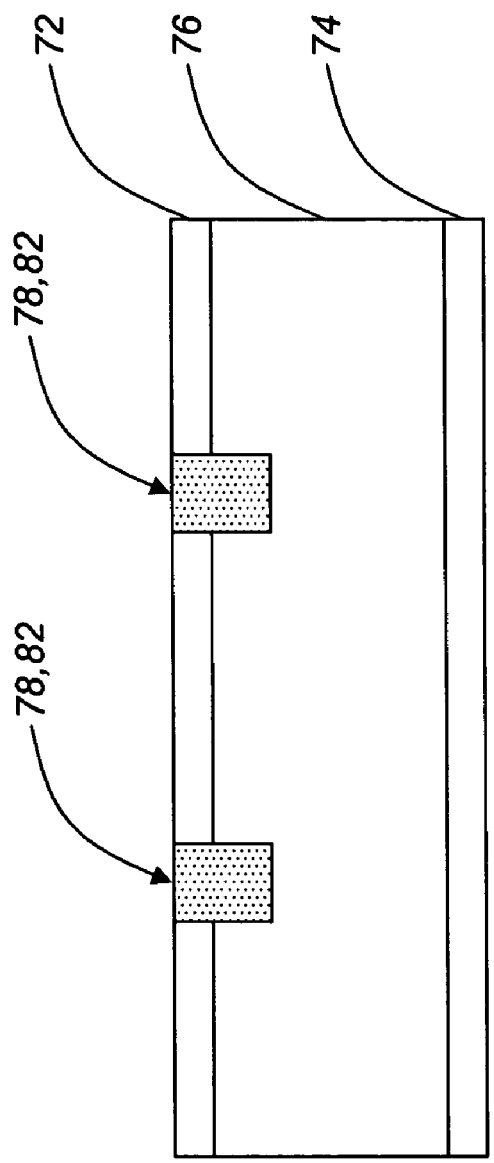
FIG. 21 is a cross-sectional side view illustrating the third step of the thick oxide approach using the thermal oxidation of high-aspect ratio trenches (HARTs) or grids of FIG. 18.

Referring to FIG. 21, the third step of the thick oxide approach using the thermal oxidation of high-aspect ratio trenches (HARTs) or grids includes the thermal oxidation of the high-aspect ratio trenches (HARTs) or grids 78 to form a thick oxide 82 within each of the high-aspect ratio trenches (HARTs) or grids 78. The thickness of this thick oxide is determined by the etched depth and is between about 1 micron and about 1,000 microns, depending upon the etching technology used. The oxidation time is determined by the spacing between the high-aspect ratio micro/nanostructures 78. For example, a 2-micon spacing between the high-aspect ratio micro/nanostructures 78, a time of approximately 10 hrs is required to close the space.

Figure 22:
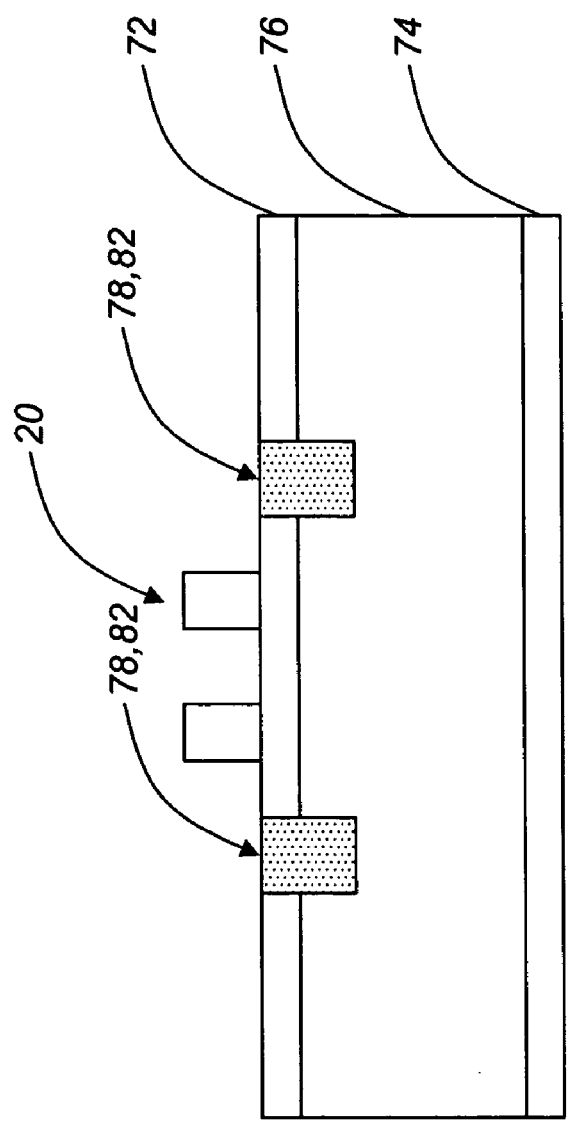
FIG. 22 is a cross-sectional side view illustrating the fourth step of the thick oxide approach using the thermal oxidation of high-aspect ratio trenches (HARTs) or grids of FIG. 18.

Referring to FIG. 22, the fourth step of the thick oxide approach using the thermal oxidation of high-aspect ratio trenches (HARTs) or grids includes selectively depositing and patterning the plurality of thin film heater/thermometers, as described above, on or adjacent to the surface of the first thin film dielectric layer 72. This is done using a second mask (not shown). As described above, the plurality of thin film heater/thermometers 20 may include a metal, polysilicon, heavily-doped silicon, silicon carbide, or the like.

Figure 23:
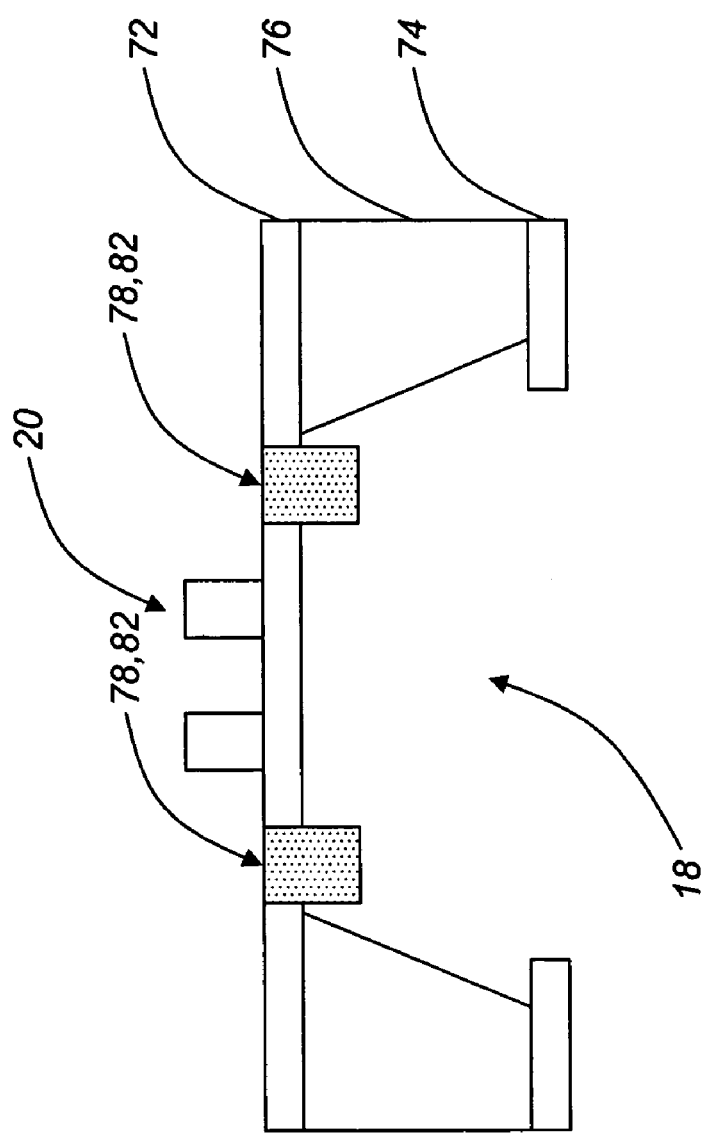
FIG. 23 is a cross-sectional side view illustrating the fifth step of the thick oxide approach using the thermal oxidation of high-aspect ratio trenches (HARTs) or grids of FIG. 18.

Referring to FIG. 23, the fifth step of the thick oxide approach using the thermal oxidation of high-aspect ratio trenches (HARTs) or grids includes patterning and selectively etching the second thin film dielectric layer 74 and the silicon layer 76 to form one or more of cells 18 described above. This is done using a third mask (not shown). The etching process may comprise a wet a and/or dry etching technique, such as potassium hydroxide (KOH) etching, tetramethylammonium hydroxide (TMAH) etching, ethylene diamine pyrocatechol (EDP) etching, and/or deep reactive ion etching (DRIE).

Figure 24:
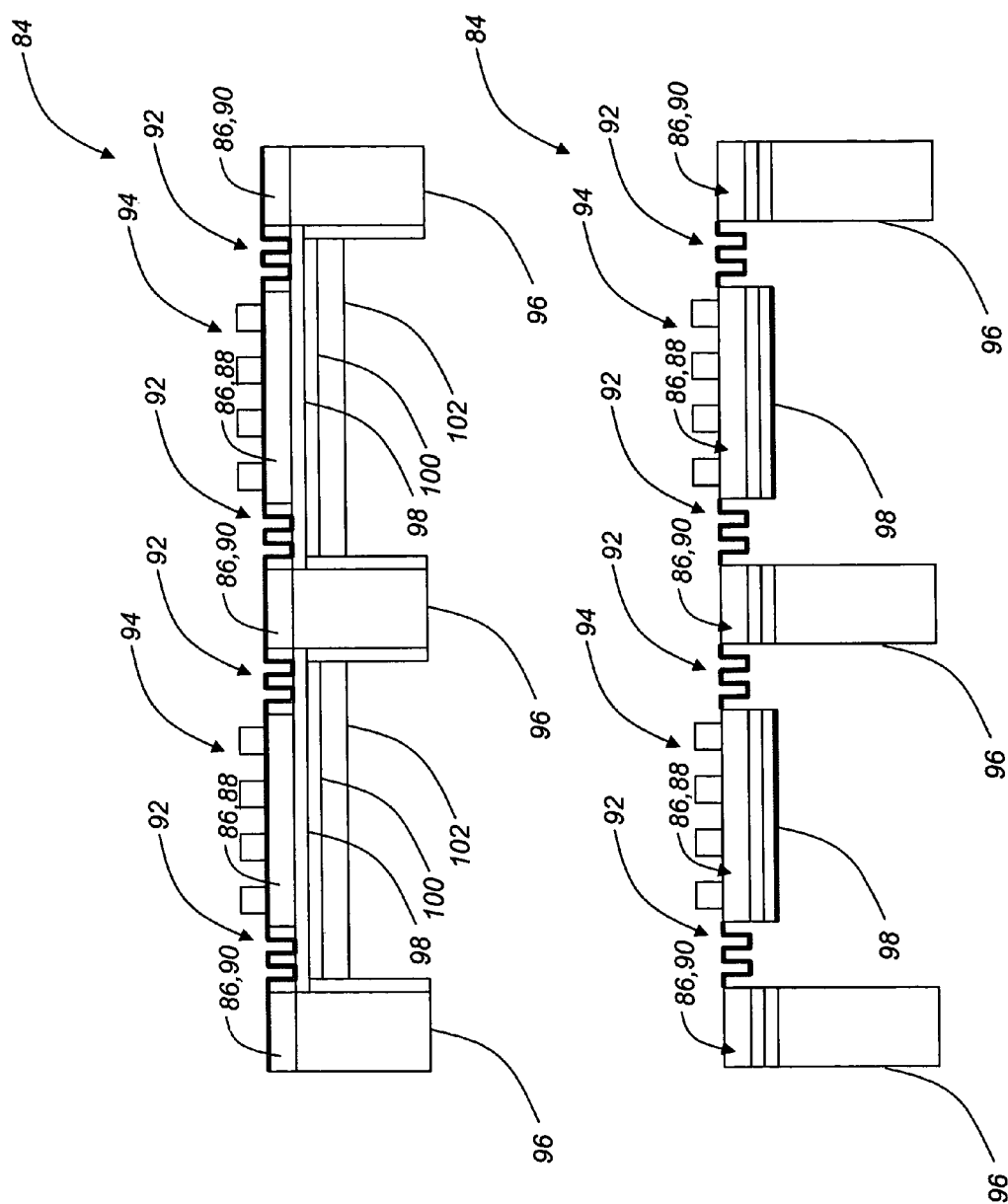
FIG. 24 is a cross-sectional side view of two related embodiments of the micro-machined humidity sensor device of the invention that utilizes high-aspect ratio silicon microstructures adjacent to the thin membranes, highlighting the sensing film prior to water adsorption.

Referring to FIG. 24, two related embodiments of the micro-machined humidity sensor device 84 of the invention that utilize high-aspect ratio silicon micro/nanostructures adjacent to the thin membranes include a thin film dielectric layer or multi-layer 86, which may include, for example, a nitride, an oxide, polysilicon, heavily-doped silicon, silicon oxinitride, an oxide/silicon/oxide multi-layer, a nitride/oxide/nitride multi-layer, a nitride/silicon/nitride multi-layer, or the like. Preferably, the thin film dielectric layer or multi-layer 86 has a thickness of between about 0.1 microns and about 5 microns, although other suitable dimensions may be used. The thickness of each layer of the thin film dielectric layer or multi-layer 86 may be selected to achieve a stress-compensated membrane. The thin film dielectric layer or multi-layer 86 is physically divided into active membrane areas 88 and inactive membrane or supporting areas 90. These active membrane areas 88 and inactive membrane or supporting areas 90 are separated by a plurality of microstructures 92 with large thermal resistances built on the peripheries of active membrane areas 88, as described above. The microstructures 92 may be deposited as a layer using, for example, a low-pressure chemical vapor deposition (LPCVD), plasma-enhanced chemical vapor deposition (PECVD), or spin-on coating technique, well known to those of ordinary skill in the art. The microstructures 92 may include an oxide, a glass, a polyimide, a polymer, a nitride, or any other suitable low-thermal conductivity material. Additionally, an oxide/nitride/oxide or nitride/oxide/nitride may be deposited for stress compensation to reduce undesirable residual thermal stresses. A plurality of metal, polysilicon, or heavily-doped silicon thin film heater/thermometers 94 are disposed adjacent to a first surface of the thin film dielectric layer or multi-layer 86 in locations corresponding to the active membrane areas 88. Further, a silicon frame 96 is disposed adjacent to a second surface of the thin film dielectric layer 86 in locations corresponding to the inactive membrane or supporting areas 90.

A thin silicon layer or self-assembled monolayer (SAM) 98 is disposed adjacent to a second surface of the thin film dielectric layer or multi-layer 86 in locations corresponding to the active membrane areas 88 and the microstructures 92. Preferably, the silicon layer or self-assembled monolayer (SAM) 98 has a thickness of between about 1 nm and about 10 nm, although other suitable dimensions may be used. A conformal nitride or oxide layer 100 is then disposed adjacent to the exposed portions of the thin silicon layer 98 and the silicon frame 96, in the case that a thin silicon layer 98 is used. Finally, a sensing film 102, such as one of the sensing films described above, a polymer, or the like, is disposed adjacent to at least a portion of the thin silicon layer 98 or conformal nitride or oxide layer 100. Preferably, the sensing film 102 has a thickness of between about 0.01 microns and about 5 microns prior to water adsorption, although other suitable dimensions may be used.

The self-assembled monolayer (SAM) 98 is disposed adjacent to the second surface of the thin film dielectric layer or multi-layer 86, in part, by depositing a high-surface area layer of silicon oxide onto a nitride diaphragm. Optionally, for a dirty silicon oxide layer, the silicon oxide layer is exposed to a piranha solution at about 50 degrees C. for about 30 minutes, making sure that the metal serpentine heater used is not exposed to the piranha solution by exclusion or masking. In a dry box, a microelectromechanical systems (MEMS) die is dried at about −50 degrees C. dew point or less with dry nitrogen or dry air purge gas at about 100 degrees C. for about 5 hours or more. The die is then immersed in a 0.5–1.0% (w/v) solution of 2-(4-chlorosulfonylpheyl)ethyltrichlorosilane in anhydrous toluene and allowed to react for about 2 hours at about 70 degrees C. The die is then rinsed in anhydrous toluene, followed by anhydrous acetone. The die is then immersed in de-ionized water at room temperature with gentle stirring for about 5 hours. The die is then rinsed in de-ionized water. Finally, the die is dried with dry air purge gas at room temperature for about 3 hours before packaging.

Figure 25:
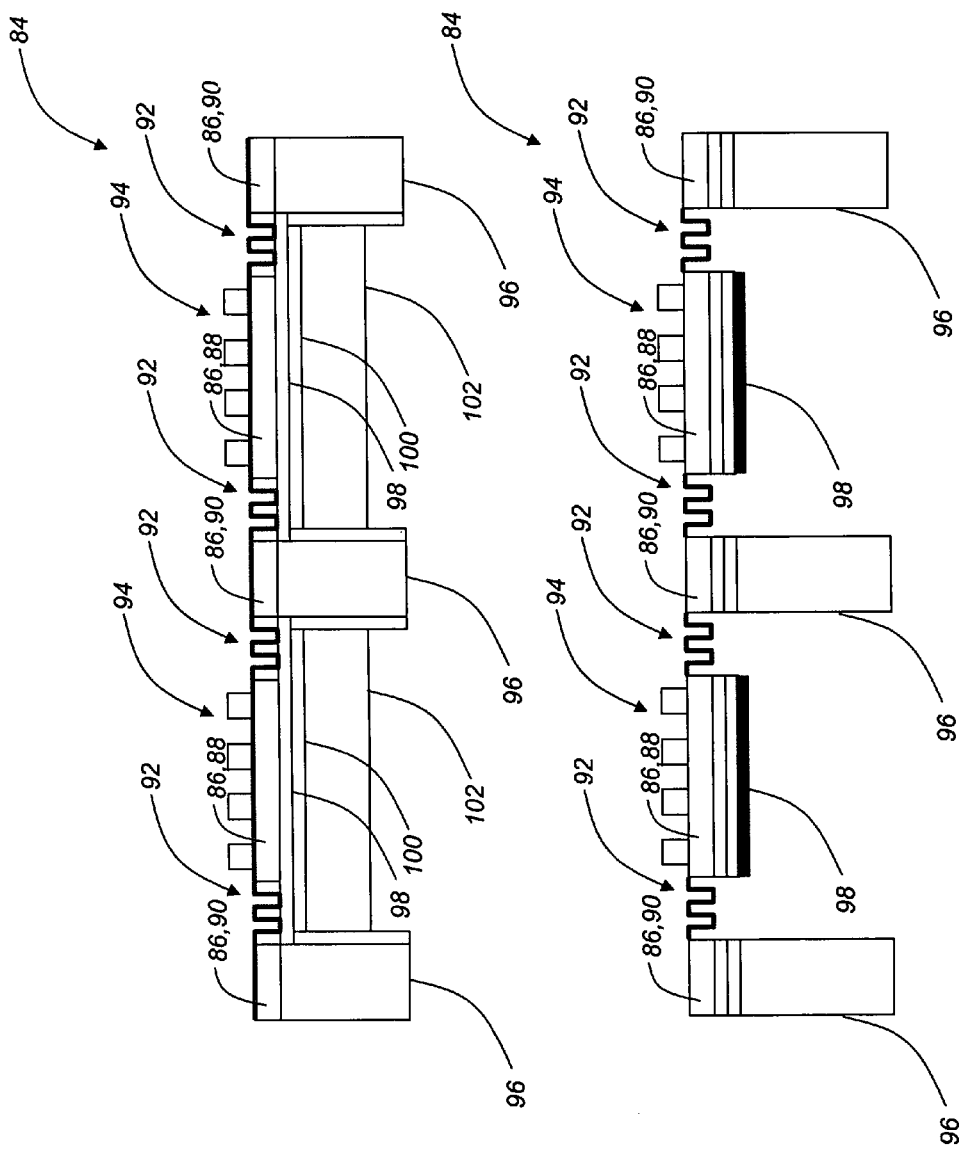
FIG. 25 is a cross-sectional side view of the micro-machined humidity sensor device of FIG. 24, highlighting the sensing film subsequent to water adsorption.

Advantageously, the silicon layer or self-assembled monolayer (SAM) 98 described above serves as a stress reliever because of the large Young's modulus coefficient of silicon and no extra stresses are generated in this layer upon the adsorption/desorption of the sensed substance. The conformal nitride or oxide layer 100 is sometimes required because it does not react with water at elevated temperatures. When the self-assembled monolayer (SAM) 98 or sensing film 102 adsorbs water, it swells and generates stresses. If the sensing film 102, for example, is deposited directly on the second surface of the thin film dielectric layer 86 in the active membrane areas 88, the thin film dielectric layer 86 may be broken due to these generated stresses. Using the devices and methods of the invention, the swollen sensing film 102, confined by the silicon layer 98, swells towards the environment. This process is illustrated in FIG. 25. Further, the silicon layer 98 and conformal nitride or oxide layer 100 provide a large surface area for the deposition of the sensing film 102 and effective heat conducting paths to the plurality of thin film heater/thermometers 94. Thus, the sensitivity and response time of the humidity sensor device 84 are significantly increased.

Figure 26:
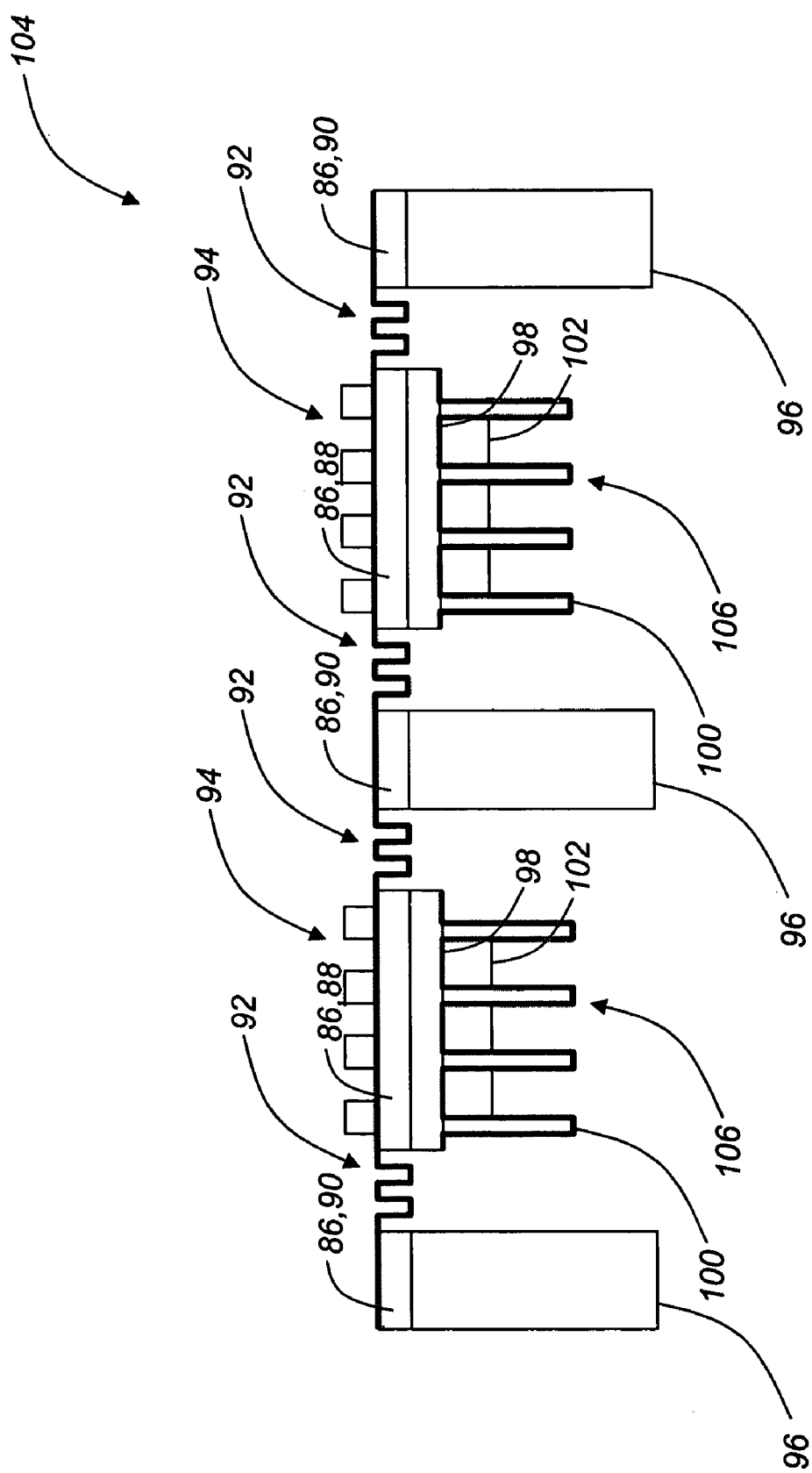
FIG. 26 is a cross-sectional side view of another embodiment of the micro-machined humidity sensor device of the invention that utilizes high-aspect ratio silicon microstructures adjacent to the thin membranes, highlighting the sensing film prior to water adsorption.

Referring to FIG. 26, another embodiment of the micromachined humidity sensor device 104 of the invention that utilizes high-aspect ratio silicon microstructures adjacent to the thin membranes also includes a thin film dielectric layer 86, which may include, for example, silicon oxinitride. Alternatively, the thin film dielectric layer 86 may include polysilicon or heavily-doped silicon. Preferably, the thin film dielectric layer 86 has a thickness of between about 0.1 microns and about 5 microns, although other suitable dimensions may be used. The thin film dielectric layer 86 is physically divided into active membrane areas 88 and inactive membrane or supporting areas 90. These active membrane areas 88 and inactive membrane or supporting areas 90 are separated by a plurality of microstructures 92 with large thermal resistances built on the peripheries of active membrane areas 88, as described above. The microstructures 92 may be deposited as a layer using, for example, a low-pressure chemical vapor deposition (LPCVD), plasma-enhanced chemical vapor deposition (PECVD), or spin-on technique, well known to those of ordinary skill in the art. The microstructures 92 may include an oxide, a glass, a polyimide, a polymer, a nitride, or any other suitable low-thermal conductivity material. Additionally, an oxide/nitride/oxide or nitride/oxide/nitride may be deposited for stress compensation to reduce undesirable thermal stresses. A plurality of metal, polysilicon, or heavily-doped silicon thin film heater/thermometers 94 are disposed adjacent to a first surface of the thin film dielectric layer 86 in locations corresponding to the active membrane areas 88. Further, a silicon frame 96 is disposed adjacent to a second surface of the thin film dielectric layer 86 in locations corresponding to the inactive membrane areas 90.

A thin silicon layer 98 is disposed adjacent to a second surface of the thin film dielectric layer 86 in locations corresponding to the active membrane areas 88. Preferably, the silicon layer 98 has a thickness of between about 1 nm and about 10 nm, although other suitable dimensions may be used. A plurality of substantially-parallel, high-aspect ratio silicon microstructures 106 are then disposed adjacent to the silicon layer 98, in a substantially-perpendicular alignment with the silicon layer 98. Preferably, each of the plurality of silicon microstructures 106 has a length of between about 0.01 microns and about 10 microns, a width of between about 0.01 microns and about 10 microns, and a depth of between about 0.01 microns and about 50 microns, although other suitable dimensions may be used. A conformal nitride or oxide layer 100 is then disposed adjacent to the exposed portions of the thin silicon layer 98 and the plurality of silicon microstructures 106. Preferably, the conformal nitride or oxide layer 100 has a thickness of between about 0.01 microns and about 1 micron, although other suitable dimensions may be used. Finally, a sensing film 102, such as one of the sensing films described above, a polymer, or the like, is disposed adjacent to at least a portion of the conformal nitride or oxide layer 100, between the plurality of silicon microstructures 106. Preferably, the sensing film 102 has a thickness of between about 0.01 microns and about 50 microns prior to water adsorption, although other suitable dimensions may be used.

Figure 27:
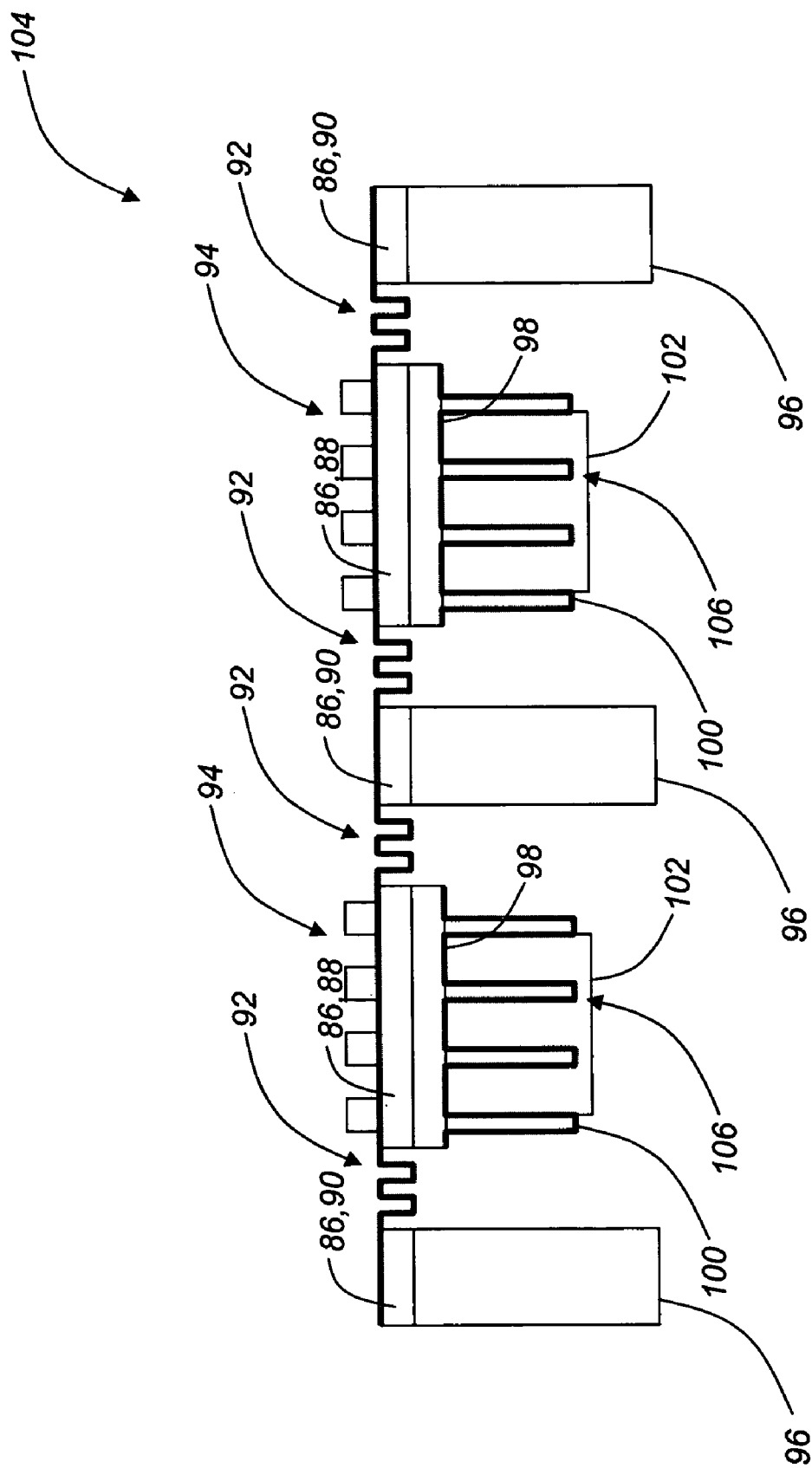
FIG. 27 is a cross-sectional side view of the micro-machined humidity sensor device of FIG. 26, highlighting the sensing film subsequent to water adsorption.

Advantageously, the silicon layer 98 and the plurality of silicon microstructures 106 described above serve as stress relievers because of the large Young's modulus coefficient of silicon. The conformal nitride or oxide layer 100 is sometimes required because it does not react with water at elevated temperatures. When the sensing film 102 adsorbs water, it swells and generates stresses. If the sensing film 102 is deposited directly on the second surface of the thin film dielectric layer 86 in the active membrane areas 88, the thin film dielectric layer 86 may be broken due to these generated stresses. Using the devices and methods of the invention, the swollen sensing film 102, confined by the silicon layer 98 and the plurality of silicon microstructures 106, swells towards the environment. This process is illustrated in FIG. 27. Further, the silicon layer 98, plurality of silicon microstructures 106, and conformal nitride or oxide layer 100 provide a large surface area for the deposition of the sensing film 102 and effective heat conducting paths to the plurality of thin film heater/thermometers 94. Thus, the sensitivity and response time of the humidity sensor device 104 are significantly increased.

In general, the multi-gas and vapor sensor devices of the invention may be used in, but are not limited to, the following exemplary applications: humidity or toxic gas monitoring for the ventilation systems of structures, emissions monitoring for automotive engine control, environmental conditions monitoring for shipping containers, hazardous or bio-warfare agent monitoring for transportation security, humidity monitoring for appliances, fire detection and response systems, disposable weather monitoring and forecasting systems, measuring the alcohol content of a human's breath, minimally-invasive blood glucose monitoring systems, monitoring human airways gas for medical and disease diagnosis, food and agricultural packaging and shipping systems, monitoring on-chip humidity for electronic circuits, monitoring humidity or chemical leaks for pressure vessels and containers, immobilization and manipulation systems for cells and proteins, medical instrumentation systems, paper production systems, semiconductor process monitoring systems, natural resource exploration and development systems, and the like.

Although the invention has been illustrated and described with reference to preferred embodiments and examples thereof, it will be readily apparent to those of ordinary skill in the art that other embodiments and examples may perform similar functions and/or achieve similar results. All such equivalent embodiments and examples are within the spirit and scope of the invention and are intended to be covered by the following claims.

What is claimed is:

1. A miniaturized sensor device, comprising:
    a thin film membrane having a first surface and a second surface;
    one or more resistive thin film heater/thermometer devices disposed directly or indirectly adjacent to a least one of the first surface of the thin film membrane and the second surface of the thin film membrane;
    a frame disposed directly or indirectly adjacent to the second surface of the thin film membrane, wherein one or more internal surfaces of the frame define at least one cell having at least one opening;
    a thin film layer disposed directly or indirectly adjacent to the frame; and
    a sensing layer disposed directly or indirectly adjacent to the thin film membrane, said sensing layer comprising a plurality of nano-scale particles and a plurality of nanopores, wherein said sensing layer serves as an interface between the sensor device and a substance being sensed.

2. The sensor device of claim 1, wherein the thin film membrane comprises a material selected from the group consisting of at least one dielectric material, polysilicon, and a combination of at least one of the foregoing materials.

3. The sensor device of claim 2, wherein the at least one dielectric material comprises a material selected from the group consisting of silicon, silicon oxinitride, parylene, polyimide, and a combination of at least one of the foregoing materials.

4. The sensor device of claim 1, wherein the thin film membrane has a thickness of between about 50 nm and about 5 microns.

5. The sensor device of claim 1, wherein the one or more resistive thin film heater/thermometer devices each comprise a material selected from the group consisting of at least one metal, polysilicon, heavily-doped silicon, silicon carbide, and a combination of at least one of the foregoing materials.

6. The sensor device of claim 5, wherein the at least one metal comprises at least one of platinum, titanium, gold, chromium, nickel, copper, and aluminum.

7. The sensor device of claim 1, wherein each of the one or more resistive thin film heater/thermometer devices has a thickness of between about 1 nm and about 50 microns.

8. The sensor device of claim 1, wherein the frame comprises a silicon frame.

9. The sensor device of claim 1, wherein the frame has a thickness of between about 50 microns and about 650 microns.

10. The sensor device of claim 1, wherein the thin film layer comprises a material selected from the group consisting of at least one dielectric material, polysilicon, parylene, polyimide, silicon oxinitride, and a combination of at least one of the foregoing materials.

11. The sensor device of claim 1, wherein the thin film layer has a thickness of between about 50 nm and about 5 microns.

12. The sensor device of claim 1, wherein the sensing layer is disposed directly or indirectly adjacent to the first surface of the thin film membrane.

13. The sensor device of claim 1, wherein the sensing layer is disposed directly or indirectly adjacent to the second surface of the thin film membrane.

14. The sensor device of claim 1, wherein the plurality of nano-scale particles comprises at least one of a plurality of nano-scale spheres, a plurality of nano-scale rods, and a plurality of nano-scale hollow fibers.

15. The sensor device of claim 1, wherein the sensing layer comprises a material selected from the group consisting of zeolite, a cross-linked organic polyelectrolyte, a self-assembled monolayer of ionic character, an aluminosilicate, a carbon nanostructure, and a combination of at least one of the foregoing materials.

16. The sensor device of claim 1, wherein the sensing layer has a thickness of between about 1 nm and about 5 microns.

17. The sensor device of claim 1, further comprising:
    an additional tin film membrane disposed directly or indirectly adjacent to the thin film layer;
    an additional frame disposed directly or indirectly adjacent to the additional thin film membrane, wherein one or more internal surfaces of the additional frame define at least one additional cell having at least two additional openings;
    a porous grid structure disposed substantially within at least one of the two additional openings of the at least one additional cell defined by the one or more internal surfaces of the additional frame; and
    an additional thin film layer disposed directly or indirectly adjacent to the additional frame.

18. The sensor device of claim 17, wherein the additional thin film membrane comprises a material selected from the group consisting of at least one dielectric material, polysilicon, and a combination of at least one of the foregoing materials.

19. The sensor device of claim 18, wherein the at least one dielectric material comprises a material selected from the group consisting of silicon, silicon oxinitride, parylene, polyimide, and a combination of at least one of the foregoing materials.

20. The sensor device of claim 17, wherein the additional thin film membrane has a thickness of between about 50 nm and about 5 microns.

21. The sensor device of claim 17, wherein the additional frame comprises an additional silicon frame.

22. The sensor device of claim 17, wherein the additional frame has a thickness of between about 50 microns and about 650 microns.

23. The sensor device of claim 17, wherein the additional thin film layer comprises a material selected from the group consisting of at least one dielectric material, polysilicon, parylene, polyimide, silicon oxinitride, and a combination of at least one of the foregoing materials.

24. The sensor device of claim 17, wherein the additional thin film layer has a thickness of between about 50 nm and about 5 microns.

25. The sensor device of claim 1, wherein at least a portion of the sensor device is substantially surrounded by an atmosphere comprising one of dry air and an inert gas.

* * * * *